US008520205B2

(12) United States Patent
Silcott

(10) Patent No.: US 8,520,205 B2
(45) Date of Patent: Aug. 27, 2013

(54) METHOD AND SYSTEM FOR DETECTING, CLASSIFYING AND IDENTIFYING PARTICLES

(75) Inventor: David B. Silcott, Reisterstown, MD (US)

(73) Assignee: Flir Systems, Inc., Wilsonville, OR (US)

(*) Notice: Subject to any disclaimer, the term of this patent is extended or adjusted under 35 U.S.C. 154(b) by 985 days.

(21) Appl. No.: 11/350,413

(22) Filed: Feb. 9, 2006

(65) Prior Publication Data

US 2006/0238757 A1 Oct. 26, 2006

Related U.S. Application Data

(60) Provisional application No. 60/651,379, filed on Feb. 9, 2005.

(51) Int. Cl.
*G01N 21/00* (2006.01)

(52) U.S. Cl.
USPC ........... 356/338; 356/318; 356/336; 356/343; 436/56; 436/172

(58) Field of Classification Search
None
See application file for complete search history.

(56) References Cited

U.S. PATENT DOCUMENTS

| 5,164,740 | A | 11/1992 | Ivri |
| 5,586,550 | A | 12/1996 | Ivri et al. |
| 5,701,012 | A | 12/1997 | Ho |
| 5,743,251 | A | 4/1998 | Howell et al. |
| 5,758,637 | A | 6/1998 | Ivri et al. |
| 5,895,922 | A | 4/1999 | Ho |
| 5,938,117 | A | 8/1999 | Ivri |
| 5,999,250 | A | 12/1999 | Hairston et al. |
| 6,014,970 | A | 1/2000 | Ivri et al. |
| 6,085,740 | A | 7/2000 | Ivri et al. |
| 6,194,731 | B1 | 2/2001 | Jeys et al. |
| 6,234,167 | B1 | 5/2001 | Sweeney et al. |
| 6,427,682 | B1 * | 8/2002 | Klimowicz et al. ...... 128/200.16 |
| 6,467,476 | B1 | 10/2002 | Ivri |
| 6,491,233 | B2 | 12/2002 | Nichols |
| 6,501,052 | B2 | 12/2002 | Sprinkle, Jr. et al. |
| 6,516,796 | B1 | 2/2003 | Cox et al. |
| 6,532,067 | B1 * | 3/2003 | Chang et al. .................. 356/318 |
| 6,540,154 | B1 | 4/2003 | Ivri et al. |
| 6,557,552 | B1 | 5/2003 | Nichols et al. |
| 6,568,390 | B2 | 5/2003 | Nichols et al. |
| 6,592,822 | B1 | 7/2003 | Chandler |
| 6,629,646 | B1 | 10/2003 | Ivri |
| 6,653,067 | B1 | 11/2003 | Griffey et al. |
| 6,681,998 | B2 | 1/2004 | Felter et al. |
| 6,755,189 | B2 | 6/2004 | Ivri et al. |
| 6,782,886 | B2 | 8/2004 | Carter et al. |

(Continued)

FOREIGN PATENT DOCUMENTS

| AU | 2004274855 B2 | 3/2005 |
| WO | WO-02061423 | 8/2002 |
| WO | WO-03031951 | 4/2003 |
| WO | WO-2004025268 | 3/2004 |

*Primary Examiner* — Dirk Bass
(74) *Attorney, Agent, or Firm* — McAfee & Taft

(57) ABSTRACT

A method and apparatus is disclosed for detecting, classifying and identifying airborne and non-airborne particles on an individual basis in substantially real time by directing a particle stream to react with optical reporters and markers and then exposing the stream to an excitation source such that individual particles have their multiple identifying characteristics detected.

33 Claims, 11 Drawing Sheets

(56) References Cited

U.S. PATENT DOCUMENTS

| | | |
|---|---|---|
| 6,802,456 B2 | 10/2004 | Shekarriz et al. |
| 6,814,071 B2 | 11/2004 | Klimowicz et al. |
| 6,885,440 B2 | 4/2005 | Silcott et al. |
| 6,921,020 B2 | 7/2005 | Ivri |
| 7,106,442 B2 * | 9/2006 | Silcott et al. ......... 356/338 |
| 2002/0058862 A1 * | 5/2002 | Furnas et al. ......... 600/300 |
| 2002/0096795 A1 * | 7/2002 | Chandler ......... 264/4.1 |
| 2003/0098422 A1 | 5/2003 | Silcott et al. |
| 2003/0223063 A1 | 12/2003 | Hill et al. |
| 2004/0125371 A1 | 7/2004 | Chang et al. |
| 2004/0177807 A1 | 9/2004 | Pui et al. |
| 2004/0232052 A1 * | 11/2004 | Call et al. ......... 209/143 |
| 2005/0179893 A1 * | 8/2005 | Hill ......... 356/318 |
| 2006/0019408 A1 * | 1/2006 | Waggoner et al. ......... 436/518 |

* cited by examiner

FIGURE 1
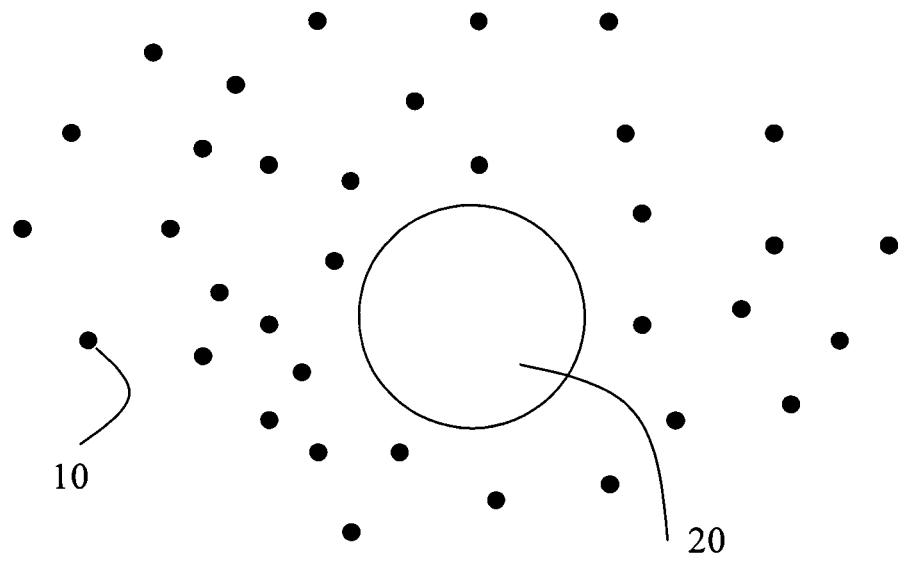
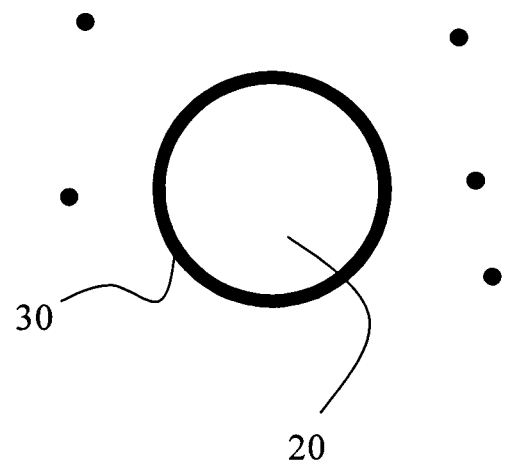

METHOD AND SYSTEM FOR DETECTING, CLASSIFYING AND IDENTIFYING PARTICLES

CROSS-REFERENCE

This application claims the benefit of U.S. Provisional Patent Application No. 60/651,379 filed Feb. 9, 2005.

FIELD OF THE INVENTION

This invention pertains generally to aerosol analyzers and more specifically to the real-time detection, classification and identification of biological and other airborne particles through the use of a particle's intrinsic optical properties and its interaction with molecular and biomolecular optical reporters.

BACKGROUND

There is a growing need for the real-time detection, classification and identification of airborne biological and non-biological particles for indoor and outdoor air quality monitoring, pulmonary patient monitoring, contagious person and animal monitoring, and for the early detection of deliberate releases of harmful aerosols such as from acts of terror or as an offensive military action.

In numerous indoor and outdoor environments there are aerosols that pose a health threat to humans. Harmful aerosols can come from numerous sources both natural and anthropogenic. The ability to monitor for the presence of such aerosols can provide a means to minimize exposure, as aerosols used as an act of terror or for offensive military use the impact can be lethal. Such harmful or lethal aerosols include types that are biological, chemical and radiological in nature.

Specific applications that require a real-time biological warning capability include battlefield defense, perimeter protection of mission critical facilities and building complexes such as military bases, facility protection against both indoor and outdoor aerosol attacks, mail biohazard screening, occupational hygiene monitoring, indoor air quality monitoring, patient monitoring of respiratory infections, etc. For each of these applications, a varied and complicated aerosol background is encountered making it a challenging problem to detect and discriminate a biological aerosol of interest from the commonly encountered aerosols for each application. Present state-of-the-art, real-time biological point detection involves sensing the auto-fluorescence of biological particulates via the excitation and detection of endogenous fluorophores and by measuring the elastic scattering of particles and/or its aerodynamic diameter using aerosol time-of-flight techniques. Techniques surrounding the extraction of auto-fluorescence, elastic scatter, and aerosol time-of-flight information from individual airborne particles are the most sensitive real-time techniques currently available. See U.S. Pat. Nos. 6,194,731; 5,999,250; 5,895,922; 5,701,012; 6,653,067; US Publication Nos. US20030223063; US20040125371; U.S. Pat. No. 6,885,440; and US Utility patent application Ser. No. 10/834,537.

The primary limitations of some known biological aerosol detection methods include the difficulty or inability in detecting airborne particulates that contain low concentrations of intrinsic fluorophores, and to discriminate from fluorescing background aerosols.

U.S. Pat. No. 6,885,440 discloses a method and apparatus for biological particle detection and classification using Mie scattering techniques and auto-fluorescence through the use of a single continuous wave laser or a laser with a modulation frequency of 50 MHz or greater. This commonly-owned patent is incorporated by reference in its entirety as if made a part of this present application.

U.S. patent application Ser. No. 10/834,537, filed Apr. 29, 2004 discloses a method and apparatus for biological particle detection and classification using elastic scattering, auto-fluorescence, and complex refractive index detection techniques through the use of one or more single continuous wave lasers and/or lasers with a modulation frequency of 20 MHz or greater. This application is incorporated by reference in its entirety as if made a part of this present application.

Therefore, a need exists for improved methods for detecting airborne biological and non-biological particulates, and for discriminating specific biological and non-biological particulates from commonly encountered background particulates.

SUMMARY OF THE INVENTION

The present invention contemplates methods, apparatuses, and systems for detecting, classifying and identifying airborne biological and non-biological particulates, in near real-time, based on the measurement of a particle's intrinsic optical properties and its interaction with molecular and/or biomolecular optical reporters. According to the present invention, combinations of five different optical phenomena are exploited: elastic scattering, absorption, fluorescence, phosphorescence and chemi-luminescence. Additionally, a means for introducing molecular and biomolecular reporters to a sampled airborne particle is provided with the subsequent interaction of such reporters with specific analyte(s) present in the aerosol particle, and with this interaction being observed through the use of elastic scattering, absorption, fluorescence, phosphorescent and/or chemi-luminescent detection techniques. The application of molecular and/or biomolecular reporters provides an additional means for enhancing the detection of airborne biological and non-biological particulates that either possess no intrinsic fluorophores or have low concentrations of intrinsic fluorophores. The use of molecular and/or biological reporters also provides a means for enhancing the discrimination of particles of interest from naturally occurring background aerosol. Further, the application of molecular and biomolecular reporters provides a means for the near real-time identification of airborne particles of interest through the proper selection of such reporters and methods for preparing sampled airborne particles so as to make available specific analytes for reaction with such reporters or reporter precursors.

Means for introducing molecular and biomolecular reporters or reporter precursors to sampled airborne particles include either by their airborne application or by their liquid application to collected airborne particles. The airborne application of such reporters or reporter precursors can be achieved by evaporation/condensation, molecular sublimation and aerosol coagulation techniques all of which provide the function of the selective and controlled deposition of such reporters or reporter precursors onto the surface of airborne particles present in sampled air. The liquid application of such reporters or reporter precursors can be achieved by first collecting sampled airborne particles using impaction or electrostatic collection techniques followed by, if needed, the liberation of specific analytes within the sampled airborne particle, and then the introduction of such optical reporters or reporter precursors. Numerous types of molecular and biomolecular reporters or reporter precursors can be utilized and can be broken down into the following types of photo-indicators: colorimetric, fluorescent, phosphorescent and chemiluminescent. Homogeneous assays and techniques used for liquid based diagnostic applications can be readily applied. Using homogeneous assays and techniques, specific biological and non-biological analytes can be measured. Table 1 provides a representative and useful though not necessarily complete list of applicable analytes.

TABLE 1

List of Analytes

Biological:

Total protein
Specific proteins
Double stranded DNA
Single stranded DNA
RNA
Specific enzymes
Specific DNA/RNA sequences
Other biological macromolecules
Molecules of biological interest
Chemical:

Organophosphates
Other organic molecules
Inorganic molecules
Radiological:

Radioactive aerosols

BRIEF DESCRIPTION OF THE DRAWINGS

FIG. 1 illustrates the coating of an airborne particle using evaporation/condensation technique.

FIG. 6 illustrates a detection system layout for the airborne application of optical reporters.

FIG. 7 illustrates the detection system layout for combined detection of non-treated and treated airborne particulates.

FIG. 8 illustrates the detection system layout for the surface detection of collected auto-fluorescent and optical reporter reacted particulates.

DETAILED DESCRIPTION OF THE INVENTION

Figure 2:
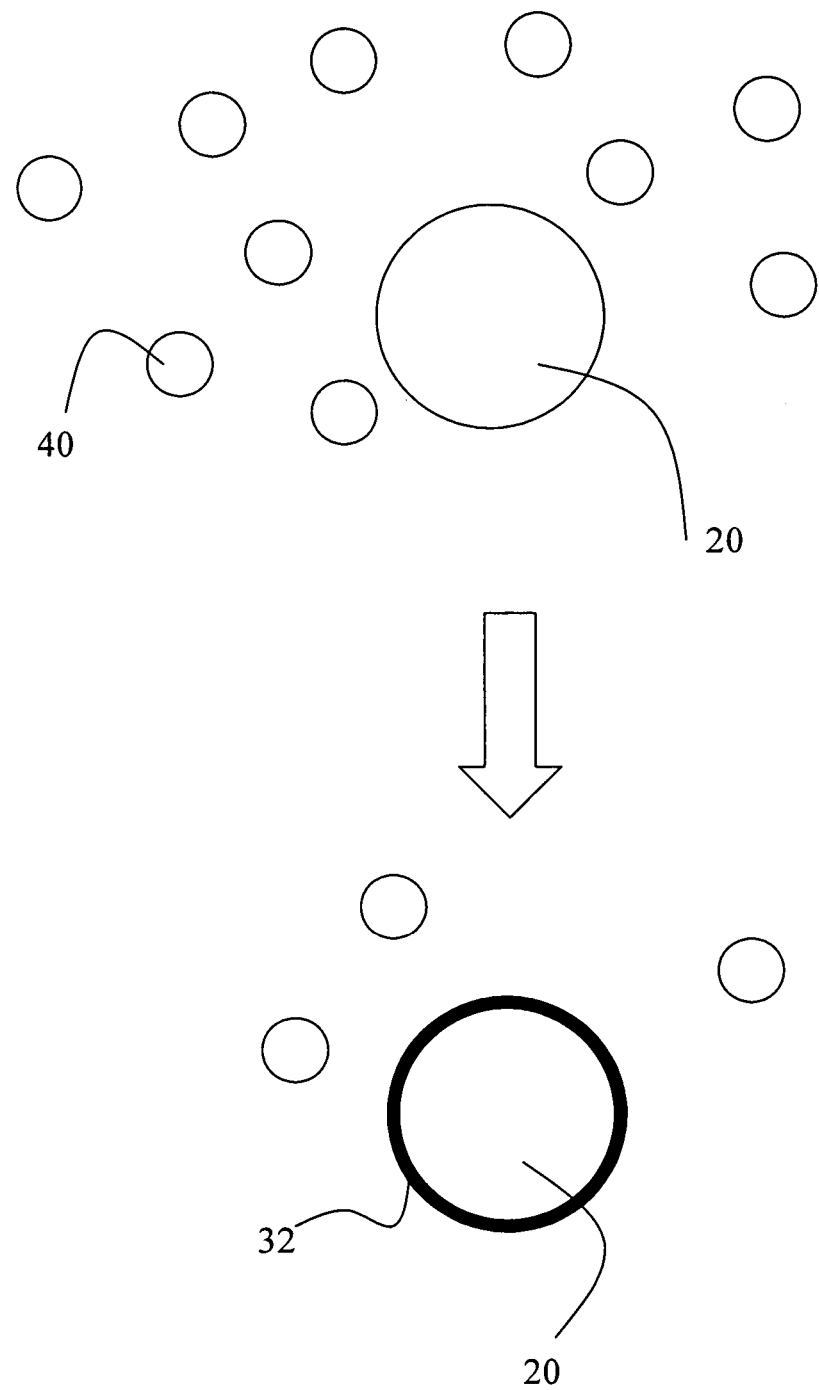
FIG. 2 illustrates the coating of an airborne particle using aerosol coagulation technique.

According to the present invention, a means for enhancing the sensitivity and specificity of aerosol detection is preferably created by combining the detection of an airborne particle's size, auto-fluorescence, or light absorptive properties with a molecular or biomolecular optical reporter(s) or reporter precursor(s). The application of molecular or biomolecular optical reporter or reporter precursor is achieved either by their airborne attachment to sampled aerosol or by their liquid introduction to collected aerosol. The combined detection of an airborne particle's size, auto-fluorescence, or absorptive properties with the reporter(s) or reporter precursors(s) is achieved either by the airborne detection or by the surface detection of reacted and non-reacted particles.

A reaction environment between the sampled airborne particles and the optical reporters is preferably created by either: 1) growing a liquid layer onto the particle's surface using an evaporation/condensation, molecular sublimation or aerosol coagulation techniques, or by 2) collecting airborne particles, and introducing collected particles to a liquid thin-film. For the airborne application of optical reporters, the thickness and chemical composition of the liquid layer can be controlled for each of the above techniques. The optimal liquid layer thickness and chemical composition can be applied depending on the homogeneous assay performed. For particles collected and then introduced to a thin-film containing optical reporters or reporter precursors, a suitable reaction environment is required that may include a means for liberation of specific analytes from the sampled airborne particle with the subsequent introduction of the optical reporter or an optical reporter precursor to the specific analyte(s).

For the airborne application of optical reporters, when using an evaporation/condensation technique, the reporter, an appropriate solvent, and other required reagents are evaporated and then introduced into a region containing the sampled aerosols. The reporter, solvent, and other required reagents are then adsorbed onto the surface of the aerosol particle. This phenomenon is known as nucleated condensation and depends on many factors that include the particle size, shape, chemical composition, surface structure and surface charge. FIG. 1 provides an illustration of the process. In this diagram, the optical reporter 10 is introduced to an aerosol sample in the form of a vapor. For soluble nuclei, condensation can occur in both supersaturated and unsaturated conditions producing droplets that are stable in size. For insoluble nuclei, when the particle diameter is greater than the Kelvin diameter, the nucleus will behave like a droplet of that size and will grow by condensation. In FIG. 1, the optical reporter 10 is introduced to an aerosol sample in the form of a vapor. The optical reporter 10 in the form of a vapor then adsorbs onto the surface of the aerosol particle 20. With sufficient adsorption, a liquid film layer 30 is then created onto the particle's surface. With this technique, the optical reporter(s) or precursor(s) then react with the appropriate markers found on the surface of the aerosol particle 20 to produce an optical reporter response based on fluorescence, phosphorescence, chemiluminescence, or a colorimetric change (change in color). A tutorial on the process of nucleated condensation can be found in "Aerosol Technology: Properties, Behavior and Measurement of Airborne Particles" by William C. Hinds.

For the airborne application of optical reporters, when using a molecular sublimation technique, the reporter, an appropriate solvent, and other required reagents are sublimed and then introduced into a region containing the sampled aerosols. As with the evaporation/condensation technique, the reporter, solvent, and other required reagents are then adsorbed onto the surface of the aerosol particle and follow the principles of nucleated condensation as described in the above paragraph.

For the airborne application of optical reporters, when using an aerosol coagulation technique, the reporter, an appropriate solvent, and other required reagents are aerosolized using electrospray or air atomization methods and other state-of-the-art aerosolization methods. Nanometer to micron size diameter-size aerosols can be generated using these methods, and these aerosols are then introduced into a region containing the sampled aerosol. The liquid aerosols then collide with the sampled aerosols, providing a means for the introduction of the reporter(s), solvent and other reagents onto the surface of the sampled aerosol particles. FIG. 2 illustrates the process. In FIG. 2, liquid aerosol containing the optical reporter(s) or precursors(s) 40 is produced using aerosol generation techniques. This aerosol is then introduced to sampled aerosol particles 20 and an environment is provided for the aerosols to coagulate. The coagulation of the liquid aerosol containing the optical reporter(s) or precursor(s) 40 with sampled aerosol particles 20 produces a liquid film 32 onto the surface of the sampled aerosol particles 20. The optical reporter(s) or precursor(s) then react with the appropriate markers found on the surface of the aerosol particle 20 to produce an optical reporter response based on either fluorescence, phosphorescence, chemi-luminescence, or a change in color. For a detailed description of aerosol coagulation, the reader is again referred to "Aerosol Technology: Properties, Behavior and Measurement of Airborne Particles" by William C. Hinds. When detecting respirable range particulates in the range of 0.5-20 micron diameter, the optimal condition for aerosol coagulation is to generate nanometer-to-micron diameter aerosols for introduction to nanometer-to-micron diameter-sampled aerosol. Coagulation will proceed faster between particles of different size than between particles of the same size. The combination of the large adsorbing surface of the sampled aerosol and the small reporter particle's rapid diffusion to the sampled aerosol's surface equates to a rapid means for applying the reporter, the appropriate solvent and the other required reagents to the sampled aerosol. For example, the coagulation between a 0.01 μm and 1.0 μm particle is 500 times more rapid than for 1.0 μm particles alone. Table 2 below provides a list of coagulation coefficients for coagulation between aerosol particles of different sizes.

TABLE 2

Coagulation Coefficients for Coagulation between Aerosol Particles of Different Sizes

| | Values of $K_{1,2}$ | | | |
|---|---|---|---|---|
| $d_1$ (μm) | $d_2 = 0.01$ μm | $d_2 = 0.10$ μm | $d_2 = 1.0$ μm | $D_2 = 10$ μm |
| 0.01 | 9.6 | 122 | 1700 | 17000 |
| 0.1 | 122 | 7.2 | 24 | 220 |
| 1 | 1700 | 24 | 3.4 | 10.3 |
| 10 | 17000 | 220 | 10.3 | 3 |

Methods for generating nanometer to micron size aerosol include electrospray and air atomization. With electrospray atomization, a nanometer to micron size diameter aerosol can be generated by operating an electrospray system in the cone-jet mode. This is achieved when a liquid meniscus supported at the tip of a capillary tube is charged to a high electric potential. Under the appropriate conditions the liquid turns into a cone whose apex emits a microscopic liquid filament that carries a certain current and flow rate. The cone-jet then breaks up into an electrospray of droplets, often in a monodisperse form, with diameter of the droplets being controlled from a diameter of a few nanometers to hundreds of microns. The size of the droplets is controlled primarily through the electrical conductivity of the liquid and the flow rate. See Rossell-Lompart and Fernandez De La Mora (1994), Kaufman et al. (1995), Fernandez De La Mora (1992), and Fernandez De La Mora and Loscertales (1994) for more detail on the process of Taylor cone generation and experimental results for different configurations. The following U.S. Patents also provide a tutorial on electrospray techniques: U.S. Pat. No. 6,802,456 and US Patent Application Publication No. 2004/0177807.

Air atomization involves the introduction of a liquid either by aspiration, gravity or pressure fed to a high velocity air stream. Under these conditions, the liquid is broken up into a polydisperse distribution of droplets with diameters spanning from tens of nanometers to hundreds of microns depending on the conditions.

Other state-of-the-art aerosol generation techniques include droplet formation via the oscillation of a metal disc containing microscopic holes, via the use of small micron-sized diameter tubes with liquid fed through at high velocities, and via heated capillary tubes. The first two techniques generate microscopic liquid filaments that break up to form monodisperse micron diameter droplets. For a tutorial on aerosol generation using an oscillating surface containing microscopic holes see U.S. Pat. Nos. 6,814,071; 6,782,886; 6,755,189; 6,629,646; 6,140,804; 6,540,154; 6,540,153; 6,467,476; 6,427,682; 6,085,740; 6,014,970; 5,938,117; 5,164,740; 5,758,637; 5,586,550. The heated capillary tube technique vaporizes a sample with subsequent condensation due to homogeneous nucleation to form aerosol. For a tutorial on submicron aerosol generation using a heated capillary tube see U.S. Pat. Nos. 6,701,921; 6,681,769; 6,681,998; 6,568,390; 6,557,552; 6,516,796; 6,501,052; 6,491,233; 6,234,167; and 5,743,251.

Figure 6:
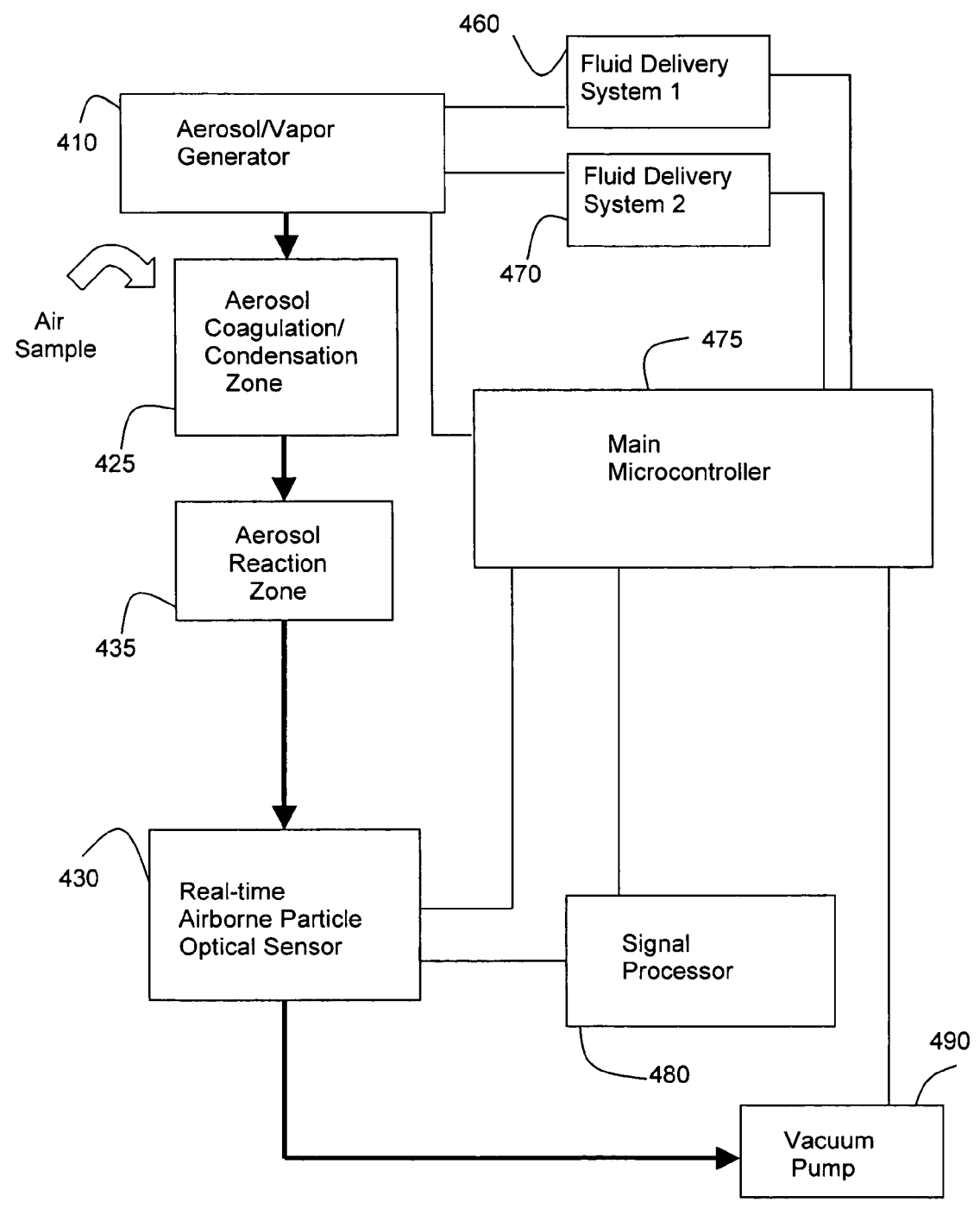

In one embodiment illustrated in FIG. 6, a detection system layout is presented that utilizes an evaporation/condensation, molecular sublimation or aerosol coagulation technique to provide the airborne application of optical reporter(s) or precursor(s). In this embodiment an aerosol or vapor generator 410 is used to produce vapor or aerosol. Optical reporter(s) or precursor(s) generated as a vapor or aerosol are then introduced into a coagulation/condensation zone 425 along with sampled aerosol particles. In this region either optical reporter or reporter precursor vapor is adsorbed onto the surface of the sampled aerosol particle or optical reporter or reporter precursor aerosol is allowed to coagulate with the sampled aerosol particles. The aerosol is then introduced into an aerosol reaction zone with dimensions and geometry to provide a delayed introduction into the real-time airborne particle optical sensor 430. A vacuum pump 490 is used to pull sampled air into the aerosol coagulation/condensation zone and into the reaction zone 435 and the real-time airborne particle optical sensor 430. One or more fluid delivery systems 460 and 470 are used to deliver the optical reporter(s) or reporter precursor(s) to the vapor or aerosol generator 410. An example of a fluid delivery system is a syringe pump containing a three port valve, automated control of the syringe pump's dispensing rate and syringe refill and a reservoir(s) for storage of the optical reporter(s) or reporter precursor(s) and the necessary support reagents. After leaving the aerosol reaction zone 435 the reacted and non-reacted particles are introduced into the real-time airborne optical sensor 430 one at a time and detected. A signal processor 480 is used to process elastic scatter and/or fluorescence, phosphorescence, or chemi-luminescence signals. The main microcontroller 475 is used to control the vacuum pump 490, aerosol/vapor generator 410, fluid delivery systems 460 and 470, and the real-time airborne optical sensor 430.

Figure 3:
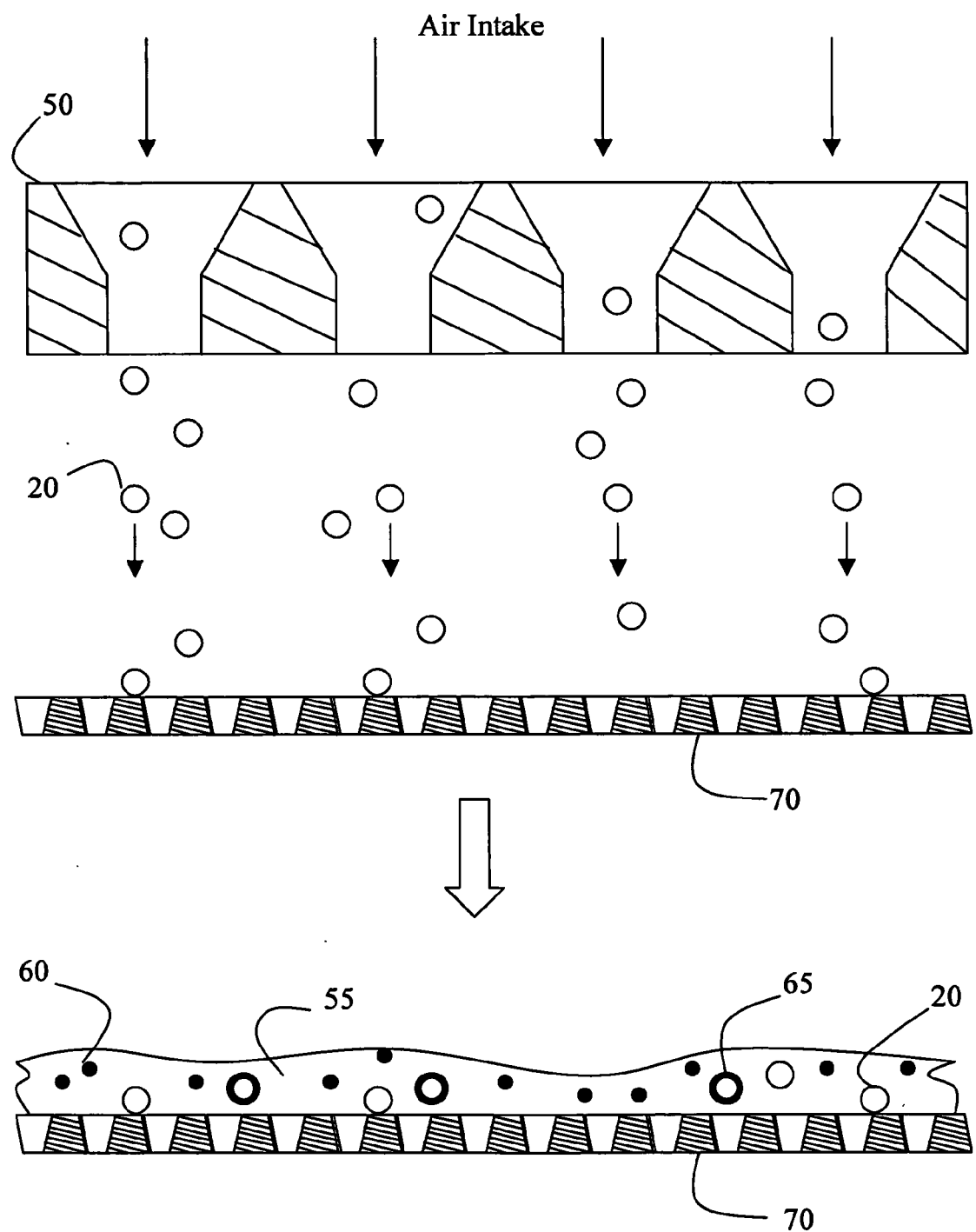
FIG. 3 illustrates the aerosol collection using inertial impaction and the liquid application of optical reporters.

For particles collected and then introduced to a thin-film, preferably of non-solid material containing optical reporters or reporter precursors, sampled aerosol particles are first collected onto a surface using electrostatic or inertial impaction techniques. It is understood that the term "non-solid" includes gels, pastes, resins, liquids, hydrogel, etc. and any material having a viscosity that is considered to not be a solid. FIG. 3 provides an illustration of the liquid application of optical reporter(s) or precursor(s) to aerosols collected using inertial impaction techniques. In this embodiment aerosol is drawn into a single or multi-nozzle impactor. The impactor is comprised of an air inlet, single or multi-nozzle for accelerating aerosol and an impaction surface. The process of inertial impaction has been thoroughly studied and for a detailed description of inertial impaction the reader is referred to "Aerosol Technology: Properties, Behavior and Measurement of Airborne Particles" by William C. Hinds. For the purposes of this invention an inertial impactor capable of collecting aerosol in the size range of 0.5-10.0 micron in diameter is desired. In FIG. 3 a multi-jet nozzle 50 is used for accelerating sampled aerosol 20 onto a collection surface, which in one embodiment, is the front surface of a planar aerosol generator 70 which is comprised of a vibratable member having a front and a rear surface, with the member having one or more tapered holes. The front surface of the planar aerosol generator 70 can either have a dry surface or a liquid thin-film 55. An example of such an aerosol generator can be found in U.S. Pat. No. 6,921,020. In this embodiment the liquid thin-film is added either before, during, or after aerosol is collected onto the surface. In another embodiment the aerosol is collected onto a dry or liquid thin-film surface and then transported to the front surface of the planar aerosol generator 70. Upon the introduction of a liquid thin-film 55 to the collected aerosol 20 the optical reporter(s) or precursor(s) 60 are then allowed to react for a predetermined period of time with the collected aerosol 20 to produces an optical reporter response on the surface of the collected aerosol particles 65 that contain the appropriate markers. The optical reporter response can be based on fluorescence, phosphorescence, chemi-luminescence, a color change, or a combination thereof. The optical reporter response and the collected particle's size, auto-fluorescence or absorptive properties can either be monitored on the surface of the planar aerosol generator 70 or can be detected in an airborne manner by re-aerosolizing the collected particles with their subsequent single particle detection.

Figure 4:
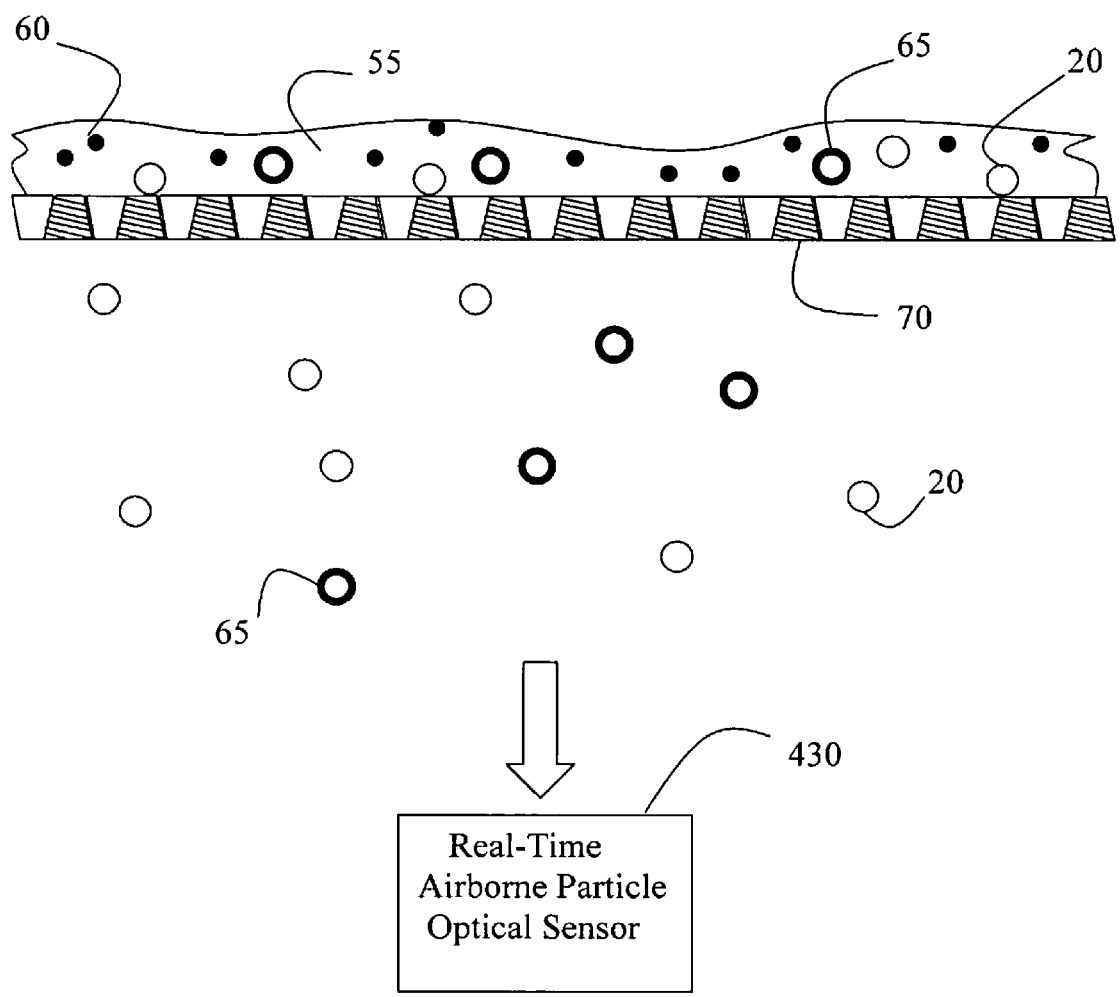
FIG. 4 illustrates the detection of re-aerosolized reacted and non-reacted particles.

As illustrated in FIG. 4, airborne detection of reacted and non-reacted collected aerosol can be achieved by re-aerosolizing the particles using the planar aerosol generator 70. The generator 70 is comprised of a vibrating member having a front and a rear surface, with the member having one or more tapered holes. When the vibrating member is oscillated, fluid is ejected from the tapered holes and efficiently aerosolizes both the liquid thin-film 55 supplied to the front surface of the generator 70, the non-reacted collected aerosols 20 and the reacted collected aerosols 65. The generator 70 aerosolizes both the collected particles and liquid thin-film very efficiently requiring only micro-liter volumes. Once re-aerosolized, the reacted and non-reacted particles are drawn into the real-time airborne particle optical sensor 430 and then detected one at a time. The generator 70 also serves as a mechanism to efficiently regenerate the impactor surface so that a large number of impacted aerosol measurements may be performed.

Figure 7:
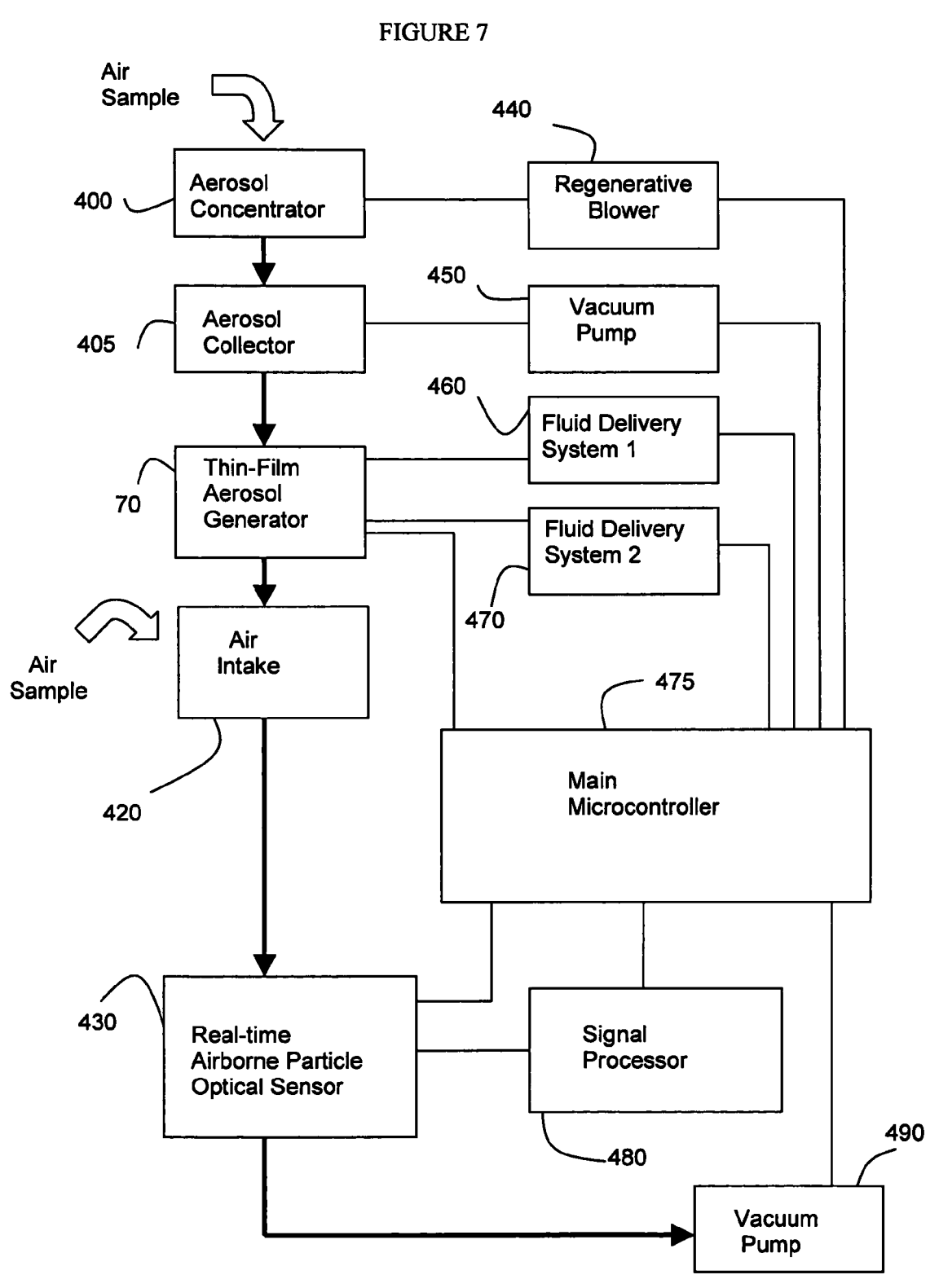

FIG. 7 illustrates a detection system layout for the combined detection of non-treated and treated airborne particulates. Depending on the application and the desired level of detection, an aerosol concentrator 400 may be used to concentrate sampled aerosol to enrich the number of particles introduced into the detection system. Using this approach a concentration factor as high as 1000 can be achieved. A regenerative blower 440 is used as the vacuum source.

The concentrated aerosol is then introduced into an aerosol collector 405 that either collects aerosol using electrostatic or inertial impaction or a combination of both. As described above sampled aerosol is then collected onto the front surface of an aerosol generator 70. A liquid thin-film is applied to the front surface of the aerosol generator 70 using one or more fluid delivery systems 460 and 470 before, during, or after aerosol is collected. An example of a fluid delivery system is a syringe pump containing a three port valve, automated control of the syringe pump's dispensing rate and syringe refill and a reservoir(s) for storage of the optical reporter(s) or reporter precursor(s) and the necessary support reagents. In a preferred embodiment, the aerosol generator's front surface is planar with a diameter less than 0.5", preferably 0.2" in diameter or less. One example is that described in U.S. Pat. No. 6,921,020. As described in the section above the generator is comprised of a vibratable member having a front and a rear surface, with the member having one or more tapered holes. A piezoceramic element is bonded to the vibratable member and when an electrically oscillating signal is applied to the piezoceramic element the vibratable member oscillates. The deflection of the vibratable member in the vertical direction forces liquid deposited onto the front surface into the tapered holes and then ejects the liquid at high velocity out of the tapered holes forming a liquid filament which breaks up into monodisperse micron size droplets. The droplet size generated is a function of the viscosity and surface tension of the liquid and the diameter of the tapered holes. The construction of the tapered holes and their diameters is controllable in the manufacturing of the vibratable element and the preferred embodiment for this invention are hole diameters that permit the re-aerosolization of 0.5 to 5 micron diameter aerosol typically, with a maximum range of 0.5 to 30 micron which equates to hole diameters that approach 5-7 micron typically with a maximum hole diameter of 30-40 micron. Oscillation frequencies of approximately 60,000 Hz can be achieved with this technique and both the pulse duration and duty cycle can be controlled electronically using microcontroller 475. It is further preferred that bonded to the rear surface of generator 70 is an annular thermal cycling device that permits the exit of aerosol from generator 70 into air intake 420 and also provides a means for both rapidly cooling and/or heating the front surface of generator 70. This capability serves as an aid in reaction kinetics for some optical reporter(s) or reporter precursors, a means for denaturing proteins and double stranded deoxyribonucleic and ribonucleic acid molecules, a means for assisting in the lysis of cellular and spore-type particles, and provides a means for performing nucleic acid type assays on the collected aerosol particles.

Using this approach, a precise and controlled delivery of an optical reporter(s) or reporter precursor(s) and supporting reagents can be delivered to the front surface of the generator 70. Additionally, precise and controlled re-aerosolization of the reacted collected aerosol 65, non-reacted collected aerosol 20 and waste supporting reagents can be achieved with pulse durations as low as 1 milli-second. With a preferred vibratable member diameter of 0.200" or less, a liquid volume of 5-30 microliters can be consistently applied and then re-aerosolized in seconds to minutes depending on the pulse duration and rates applied to the generator 70. With the use of small reagent volumes, a large dynamic range for the aerosol generation rate and the precise control liquid delivery, the detection system can be configured to provide a near continuous processing to a collected aerosol with re-aerosolization of reacted and non-reacted aerosol. The system can also be configured to be perform longer aerosol collection times and/or longer sample reaction times depending on the application and the expected analyte's concentration. The system can also be configured to detect only non-treated airborne particles measuring their size, auto-fluorescence, absorptive properties for a fixed period of time when aerosol collection is occurring with another fixed period of time where the detection system is configured to detect both or only the re-aerosolized reacted particles containing an optical reporter (s) and the non-reacted particles.

In the detection system layout illustrated in FIG. 7 sampled aerosol is also drawn into the detection system at air intake 420 for the real-time detection of non-treated aerosol using airborne particles detection techniques such as that described in U.S. Pat. No. 6,885,440 and U.S. patent application Ser. No. 10/834,537. The above patent and patent applications are incorporated by reference in their entirety, as if made a part of this present application. At air intake 420 the re-aerosolized reacted and non-reacted collected particles are introduced to the same air sample stream containing non-treated aerosol with the vacuum provided by vacuum pump 490. The combined aerosol is then drawn into the real-time airborne particle optical sensor 430. With optical sensor 430 the combined aerosol is measured one particle at a time. For the measurement of the combined aerosol, a means is provided for the simultaneous or synchronized measurement of particle size, auto-fluorescence, and luminescence produced by the optical reporter(s) either as fluorescence, phosphorescence, chemi-luminescence, or a change in color. A signal processor 480 is used to process elastic scatter and/or fluorescence, phosphorescence, or chemi-luminescence signals. The main microcontroller 475 is used to control the vacuum pump 490, aerosol generator 70, fluid delivery systems 460 and 470, and the real-time airborne optical sensor 430.

Figure 9:
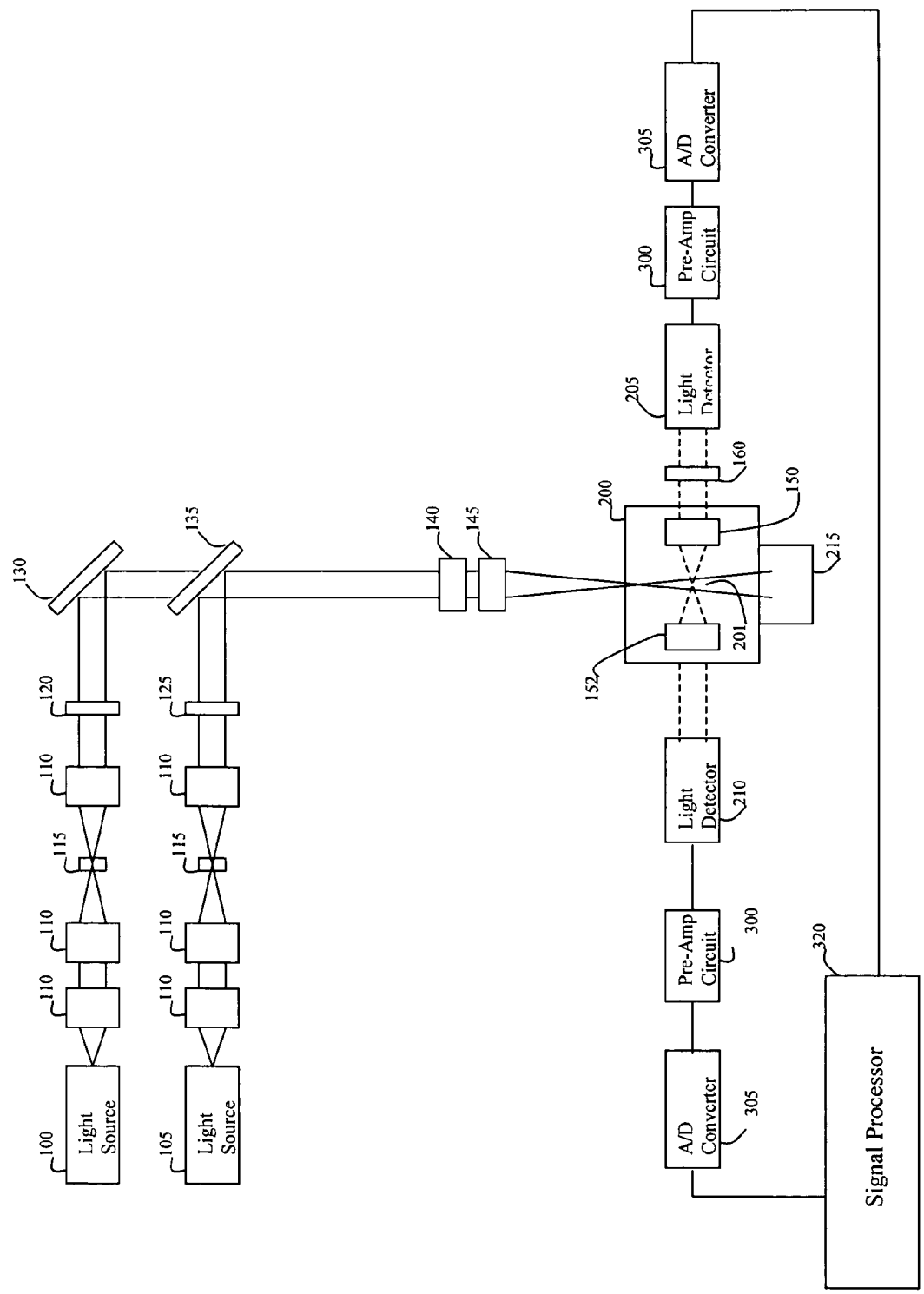
FIG. 9 is a schematic representation of one embodiment of the aerosol sensing configuration that uses a dual wavelength excitation and two elastic scatter and two auto-fluorescence/optical reporter detection channels.
Figure 10:
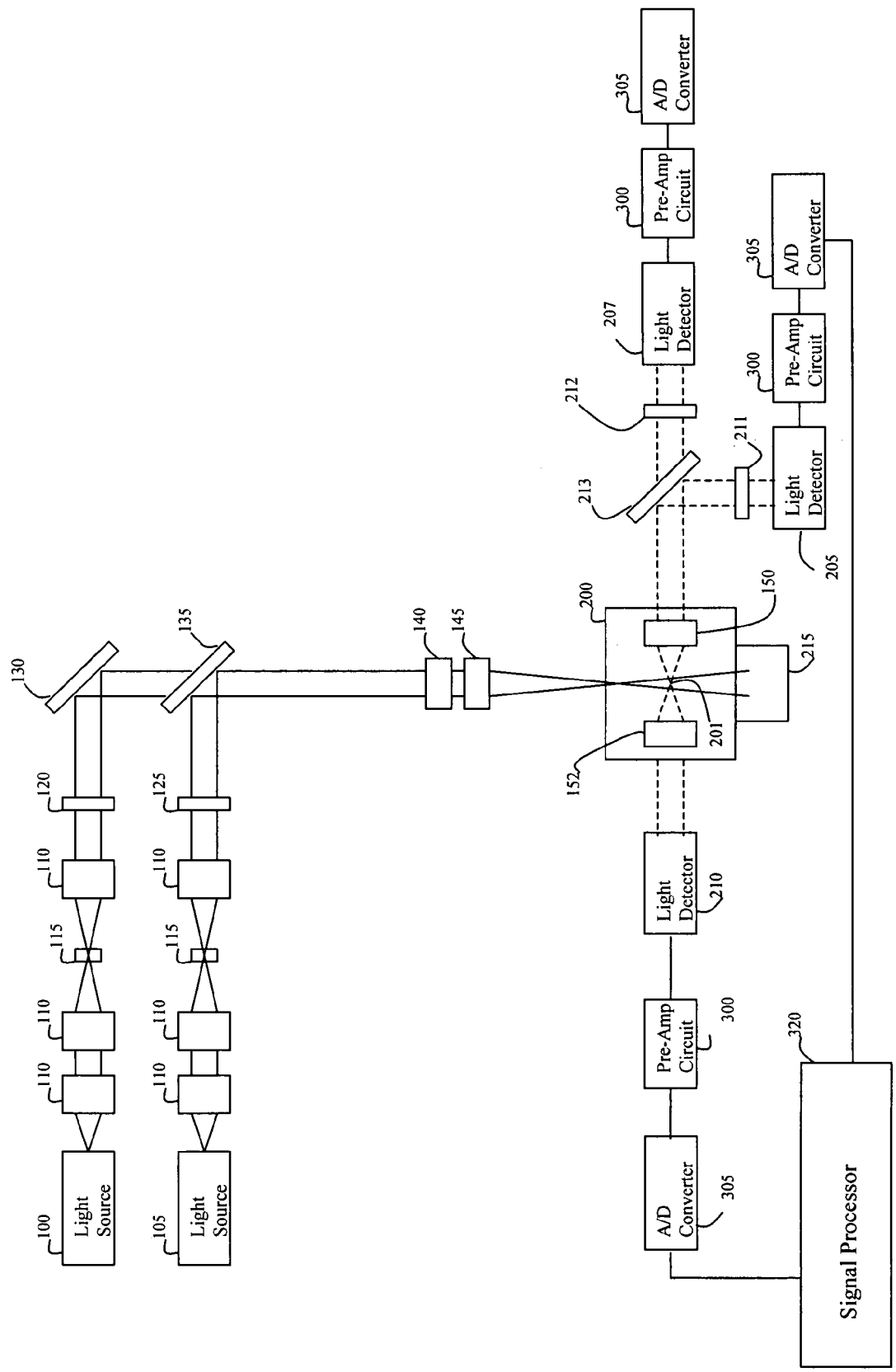
FIG. 10 is a schematic representation of one embodiment of the aerosol sensing configuration using a dual wavelength excitation and tone elastic scatter and two auto-fluorescence/optical reporter detection channels.
Figure 11:
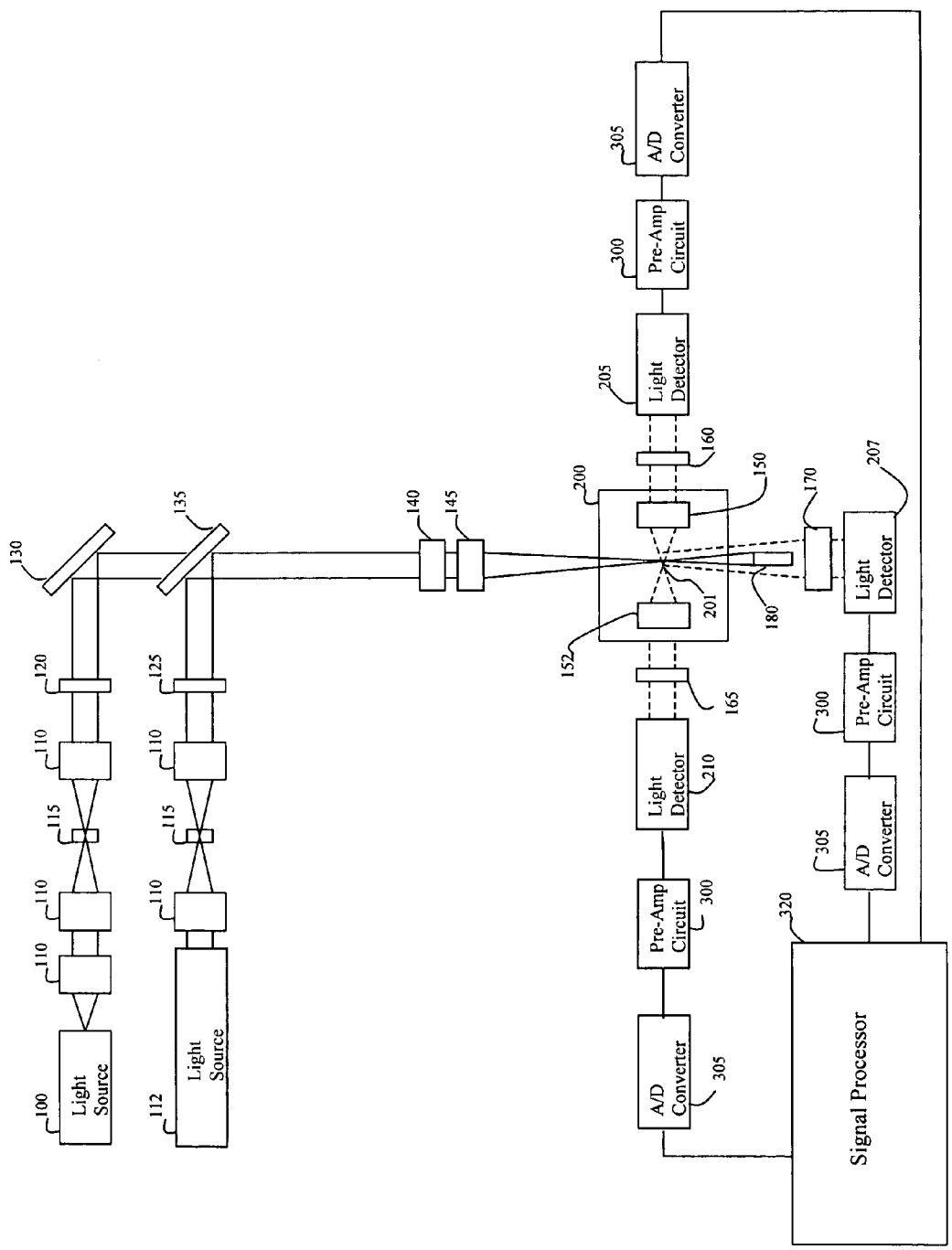
FIG. 11 is a schematic representation of another embodiment of the aerosol sensing configuration using dual wavelength excitation with near forward elastic scatter and two auto-fluorescence/optical reporter detection channels.

Described herein are three aerosol sensing configurations which are variations of two excitation wavelengths and two auto-fluorescence and/or optical reporter detection channels. Additional aerosol sensing configurations are described in U.S. Pat. No. 6,885,440 and U.S. patent application Ser. No. 10/834,537. In the three configurations, aerosol is drawn into an optical viewing region at 0.5 to 30 liters per minute and particles are illuminated one at a time with two light beams either separated in space from each other or superimposed in space with no spatial separation. FIGS. 9-11 provide block diagrams of the different configurations. In each of the configurations, the excitation wavelengths preferably can include one of the following combinations: 220-300 nm and 340-490 nm; 340-490 nm and 500-1500 nm; and 220-300 nm and 500-1500 nm. Two separate laser or LED sources can be used to provide excitation wavelengths in the above wavelength ranges, or a single laser can be used in concert with harmonic generation techniques. Additionally, one or more of the sources can operate in a modulated manner or as a continuous wave source. For the modulated sources, a modulation rate of 10 MHz or greater is preferred. For the above ultraviolet wavelength excitation ranges that includes the 220-300 nm range and partially the 340-490 nm range a harmonically generated source can be used that, preferably has a modulation rate of 10 MHz or greater. Laser line generating optics are used to generate a laser line thickness of from about 5μ to about 300μ, and a depth of field and laser line width that is at least two times (2×) the diameter of the aerosol inlet orifice employed. The optics employed generate a laser line with one of the excitation wavelengths being optically aligned on top of the other separated by a known distance or superimposed in space with no spatial separation with the two laser lines positioned orthogonal to the aerosol inlet probe. A laser line thickness of from about 5μ to about 300μ provides a means for a short aerosol migration time permitting a high-count rate and a means for high optical energy density for optimal optical power illumination.

FIG. 9 illustrates a configuration whereby two excitation sources are employed with two elastic scatter detection channels and two auto-fluorescence and optical reporter detection channels. Aerosol is drawn into the sensor cell 200 through an aerosol nozzle (not shown) and is introduced into an optical viewing region 201. Two excitation sources 100, 105 are employed. The excitation sources 100, 105 can be either a continuous source or modulated at 10 MHz or greater frequency and can be, for example, a laser, light emitting diode, or some other light emitting device, etc. Excitation source 100 is a longer wavelength than excitation source 105 in one of two wavelength ranges: 340-490 nm or 500-1500 nm. Excitation source 105 is a shorter wavelength than excitation source 100 and emits in one of two wavelength ranges: 220-300 nm or 340-490 nm. Light emitted from these sources is collimated using an aspheric lens 110 and then spatially filtered by focusing the collimated light using another aspheric lens 110 onto a pin hole aperture 115 and then re-collimated using another aspheric lens 114. Collimated light from both sources can then be introduced to narrow bandpass filters 120, 125 for removal of unwanted wavelengths emitted from sources 100 and 105 or from auto-fluorescence produced from the optical elements. Collimated light from both excitation sources 100, 105 are introduced to a mirror 130 and a dichroic mirror 135, respectively, positioned at about 45 degrees relative to the collimated light. Mirror 130 and dichroic mirror 135 provide the means for alignment of the two collimated sources onto the same optical train.

In one embodiment of the present invention, the two collimated beams are aligned to be separated by a known distance along the plane orthogonal to the aerosol inlet nozzle so that a single detector can be used to detect elastically scattered light at two different excitation wavelengths, and another single detector for detection of auto-fluorescence or reporter (s) emission at the two different excitation wavelengths. Separating the two illumination beams permits an individual particle to be illuminated at two different times but in a correlated manner.

In another embodiment, the collimated beams are superimposed in space with no spatial separation and sequentially powered so that only one source is on at a time. The switching frequency for the two sources can be configured fast enough to illuminate each particle sampled with both sources, or can be configured to illuminate a population of sampled aerosol with one source followed by the illumination of another population with the other source. The two collimated beams are aligned along the plane orthogonal to the aerosol inlet nozzle so that a single detector can be used to detect elastically scattered light at two different excitation wavelengths and another single detector for detection of auto-fluorescence emission at the two different excitation wavelengths or reporter emission.

For both embodiments, the collimated beams are then introduced to either a light exiting mirror 130 or dichroic mirror 135 and then introduced to a series a beam shaping optics creating a sheet of light at the aerosol nozzle region that is from about 5μ to about 300μ in thickness and a depth of field, and beam width that is at least about two times (2×) larger than the diameter of the aerosol inlet nozzle. In one embodiment, a spherical lens 140 and a cylindrical lens 145 are used to generate the above geometry. In one preferred embodiment of the present invention, a spherical lens 140 and a Powell lens 145 are used.

The two light beams generated from the beam shaping elements 140 and 145 are then introduced into the optical viewing region 201. Particles are illuminated, one at a time, in this region 201 with an aerosol migration time of from about 50 to about 1000 nanoseconds. Light exiting this region in the forward direction is collected using a light trap 215.

In the embodiment illustrated in FIG. 9, light both emitted as elastic scatter and as photo-luminescence is side-angle collected over the range of 65-115 degrees using light collection lenses 150, 152. The light collection lenses 150, 152 collect light emitted in the illumination region over the range of 65-115 degrees and then collimate the light for introduction to bandpass filter 160 for the fluorescence detection channel and finally to the light receiving elements (light detectors) 205 and 210. The collector lenses 150, 152 can be aspheric condensers, cylindrical lenses, or diffractive optical elements.

As shown in FIG. 9, two collector lenses 150, 152 are used in this embodiment. One is used for collecting elastically scattered light emitted by the particle from both of the excitation wavelengths, and one is used for collecting auto-fluorescence or reporter emission from the illuminated particle for each of the two excitation wavelengths. For the auto-fluorescence or optical reporter channel, a multi-band filter element 160 is used to filter out all wavelengths except for two wavelength ranges that correspond to a luminescence emission for two different auto-fluorescence emission ranges or reporter emission ranges.

Elastically scattered light is then introduced to a light receiving element (light detector) 210. The light receiving element is preferably a photomultiplier tube, avalanche photodiode, or silicon photodiode. Auto-fluorescence or optical reporter emission that passes through the multi-band filter element 160 is introduced to a single receiving element (light detector) 205 such as a photomultiplier tube, avalanche photodiode, or a silicon photodiode that has a similar sensitivity as a photomultiplier tube or avalanche photodiode. Signals from both light receiving elements 205 and 210 are then introduced to a preamplifier circuit 300 whereby a 50-1000 nanosecond current pulse is converted first to an analog voltage and then to a digital signal using an analog-to-digital converter 305. The signals from all four channels are then introduced to a signal processor 320 for analysis. The signal processor 320 can be for example, a microcontroller, digital signal processor, field programmable gate array, a microcomputer, etc., as would be readily understood by one skilled in the field of signal processing.

FIG. 10 illustrates a configuration that is similar to that illustrated in FIG. 9 but with a different light collection scheme for detecting elastic scatter, auto-fluorescence and reporter emission. In this configuration, light collected from collector lens 150 is introduced to a dichroic mirror 213 that separates the incoming light into two separate emission wavelength ranges. The emission wavelength ranges are based on which excitation wavelengths have been employed for sources 100 and 105 and what auto-fluorescence and/or reporter emission ranges are required. The separated light from dichroic mirror 213 is then introduced to two different optical filter elements 212 and 211. Optical filter element 212 is configured to pass only a wavelength that corresponds to a specific auto-fluorescence or optical reporter emission range. Optical filter element 211 is configured to only pass another wavelength range that corresponds to another specific auto-fluorescence or optical reporter emission range.

Elastically scattered light is then introduced to a light receiving element (light detector) 210. The light receiving element is a photomultiplier tube, avalanche photodiode, or silicon photodiode. In this embodiment, only a single elastic scatter channel is used in aerosol detection. Auto-fluorescence or reporter emission that passes through optical filter element 211 and 212 are introduced to receiving elements (light detector) 205 and 207, respectively, such as a photomultiplier tube, avalanche photodiode, or a silicon photodiode that has a similar sensitivity as a photomultiplier tube or avalanche photodiode. Signals from light receiving elements 205, 207 and 210 are then introduced to preamplifier circuits 300 whereby a 50-1000 nanosecond current pulse is converted first to an analog voltage and then to a digital signal using an analog-to-digital converter 305. The signals from all three channels are then introduced to a signal processor 320 for analysis. The signal processor 320 can be, for example, a microcontroller, digital signal processor, field programmable gate array, a microcomputer, etc., as would be readily understood by one skilled in the field of signal processing.

FIG. 11 illustrates a dual wavelength excitation scheme with near forward elastic scatter detection and two auto-fluorescence/reporter detection channels. Aerosol is drawn into the sensor cell 200 through an aerosol nozzle (not shown) and is introduced into an optical viewing region 201. Two excitation sources (labeled as Light Sources) 100, 112 are employed. The excitation source 100 can be either a continuous source or modulated at 10 MHz or greater frequency and can be for example, a laser, light emitting diode, or some other light emitting device, etc. Excitation source 100 is a longer wavelength than excitation source 112 in one of two wavelength ranges: 340-490 nm or 500-1500 nm. Excitation source 112 is a shorter wavelength than excitation source 100 and emits in one of two wavelength ranges: 220-300 nm or 340-490 nm. Excitation source 112 uses nonlinear harmonic conversion to produce the above ultraviolet wavelength ranges. If not already collimated, light emitted from these sources is collimated using an aspheric lens 110 and then spatially filtered by focusing the collimated light using another aspheric lens 110 onto a pin hole aperture 115 and then re-collimated using another aspheric lens 114. Collimated light from both sources can then be introduced to narrow bandpass filters 120, 125 for removal of unwanted wavelengths emitted from sources 100 and 112 or from auto-fluorescence produced from the optical elements. Collimated light from both excitation sources 100, 112 are introduced to a mirror 130 and a dichroic mirror 135, respectively, positioned at 45 degrees relative to the collimated light. Mirror 130 and dichroic mirror 135 provide the means for alignment of the two collimated sources onto the same optical train.

The collimated beams are superimposed in space with no spatial separation. The two collimated beams are aligned along the plane orthogonal to the aerosol inlet nozzle so that a single detector 207 can be used to detect elastically scattered light in the near forward direction and two other detectors another single detector for detection of auto-fluorescence emission at the two different excitation wavelengths or reporter emission.

The collimated superimposed beams are then introduced to either a light exiting mirror 130 or dichroic mirror 135, and are then introduced to a series—of a beam shaping optics, creating a sheet of light at the aerosol nozzle region that is from about 5μ to about 300μ in thickness and a depth of field and beam width that is at least about two times (2×) larger than the diameter of the aerosol inlet nozzle. In one embodiment, a spherical lens 140 and a cylindrical lens 145 are used to generate the above geometry. In one preferred embodiment of the present invention, a spherical lens 140 and a Powell lens 145 are used.

The two light beams generated from the beam shaping elements 140 and 145 are then introduced into the optical viewing region 201. Particles are illuminated, one at a time, in this region 201 with an aerosol migration time of from about 50 to about 1000 nanoseconds. Light exiting this region in the forward direction in the angular range of 0-4 degrees is collected using a light trap 180 and from 4-30 degrees is introduced to an optical filter 170 filtering out all wavelengths except for that produced by one of the excitation sources 100 or 112. Light collected in the near-forward direction over the angular range of 4-30 degrees is then introduced to light detector 209 and the signal produced is used for determination of the particle's size based on Mie scatter theory.

Two collector lenses 150, 152 are used in this embodiment to collect auto-fluorescence or reporter emission from the illuminated particle at two different wavelength ranges. For one auto-fluorescence or optical reporter emission channel, an optical filter element 212 is used to filter out all wavelengths except for a wavelength ranges that corresponds to an auto-fluorescence or optical reporter emission range. For the other auto-fluorescence or optical reporter emission channel, an optical filter element 211 is used to filter out all wavelengths except for a wavelength range that corresponds to the second auto-fluorescence or optical reporter emission range.

Auto-fluorescence or reporter emission that passes through optical filter elements 211 and 212 are introduced to receiving elements (light detector) 205 and 207, respectively, such as a photomultiplier tube, avalanche photodiode, or a silicon photodiode that has a similar sensitivity as a photomultiplier tube or avalanche photodiode. Signals from light receiving elements 205, 207 and 210 are then introduced to preamplifier circuits 300 whereby a 50-1000 nanosecond current pulse is converted first to an analog voltage and then to a digital signal using an analog-to-digital converter 305. The signals from all three channels are then introduced to a signal processor 320 for analysis. The signal processor 320 can be a microcontroller, digital signal processor, field programmable gate array or a microcomputer, as would be readily understood by one skilled in the field of signal processing.

Figure 5:
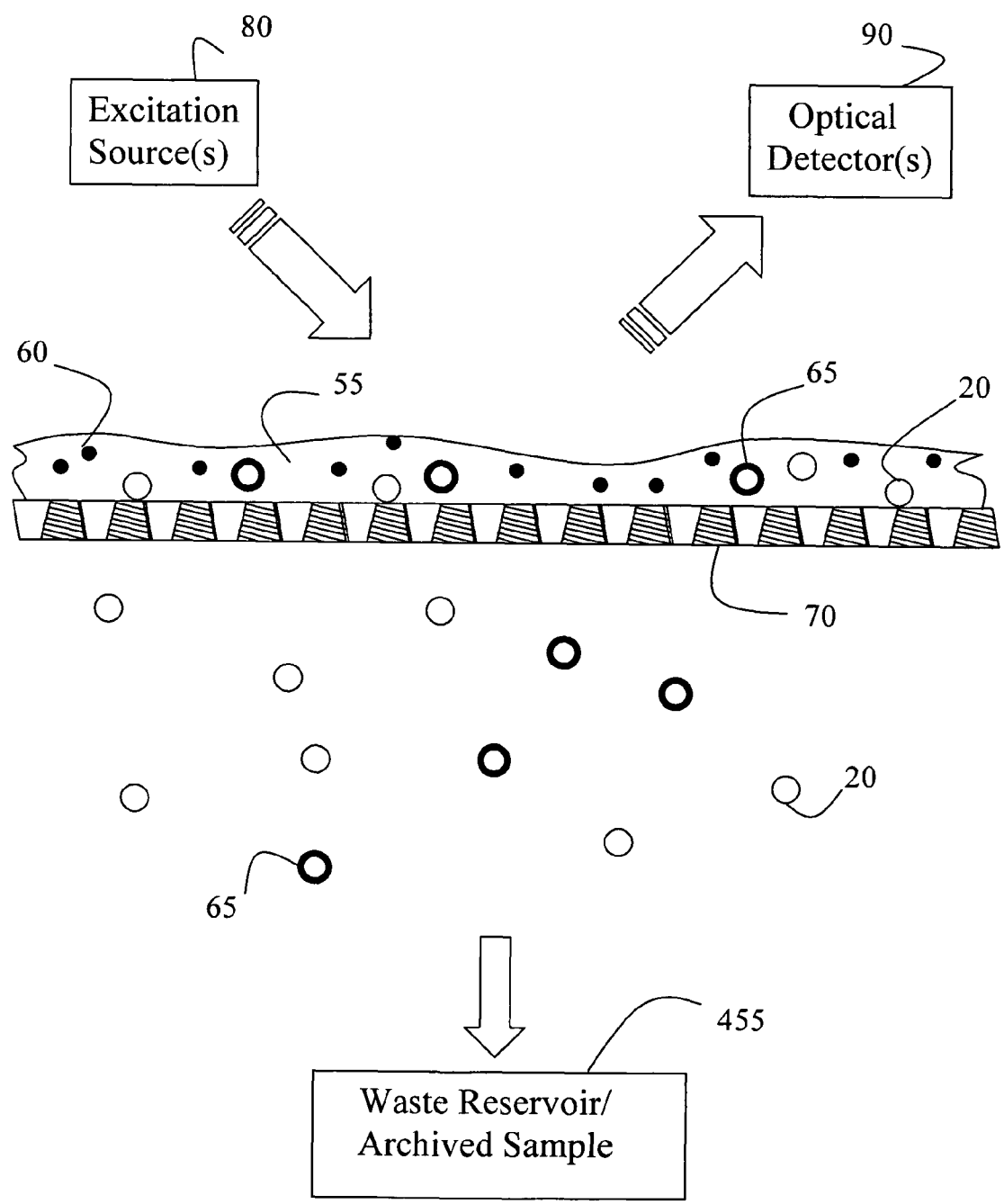
FIG. 5 illustrates the surface detection of reacted and non-reacted particles.

As illustrated in FIG. 5, surface detection of reacted and non-reacted collected aerosol particles can be achieved by the illumination with one or more excitation source(s) 80 of the front surface of the planar aerosol generator 70. The excitation source can be either a laser or light emitting diode. Optical detector(s) 90 can be positioned above the front surface of the aerosol generator 70 for detection of auto-fluorescence and/or optical reporter fluorescence, phosphorescence, or chemi-luminescence. Using this approach, as aerosol is collected, the auto-fluorescence of the collected aerosol 20 can be monitored by the illumination of the front surface of the aerosol generator 70 with one or more excitation sources 80 and the fluorescence emission is detected using one or more optical detector(s) 90. The excitation wavelength(s) are selected for optimal excitation of endogenous fluorophores commonly found in biological particles such as, for example, aromatic amino acids, nicotinamide adenine dinucleotide (NADH), flavins, chlorophyll, etc. Optimal excitation wavelengths include two excitation ranges: 220-300 nm and 340-490 nm. There are numerous light sources available for excitation of the optical reporter(s) and the selection of which source to apply is dependent on which optical reporter is used. By impacting the sampled aerosol onto the front surface of the aerosol generator 70, a means is provided for regenerating the impactor surface. The generator 70 preferably comprises a vibrating member having a front and a rear surface, with the member having one or more tapered holes. When the vibrating member is oscillated, fluid is ejected from the tapered holes and aerosolizes efficiently both the fluid supplied to the front surface of the generator 70 and the collected aerosols 20. This serves as a mechanism to efficiently regenerate the impactor surface so that a large number of impacted aerosol measurements may be performed.

Figure 8:
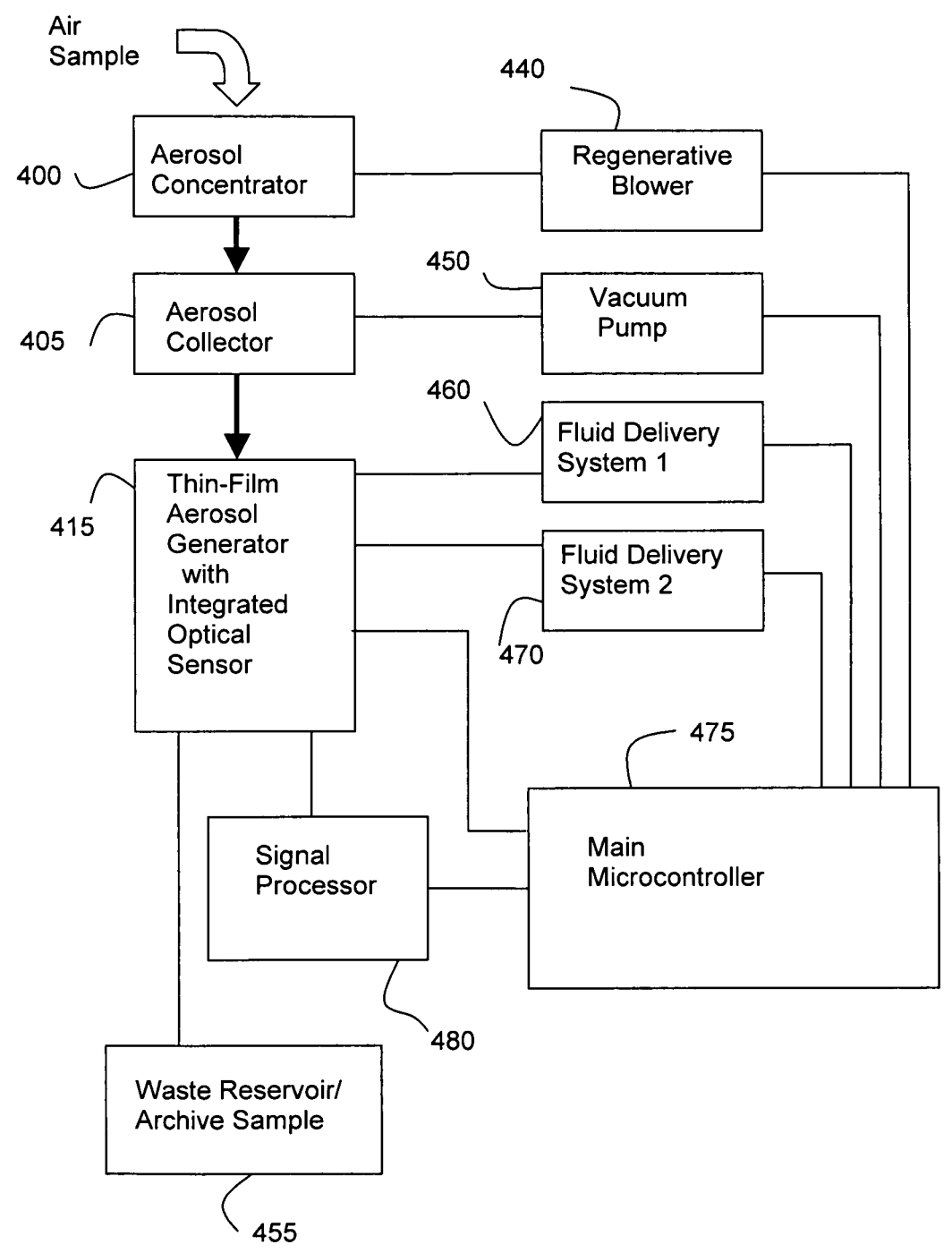

FIG. 8 illustrates a detection system layout for surface detection of collected auto-fluorescent and optical reporter reacted particulates. Depending on the application and the desired level of detection, an aerosol concentrator 400 may be used to concentrate sampled aerosol to enrich the number of particles introduced into the detection system. Using this approach a concentration factor as high as 1000 can be achieved. A regenerative blower 440 is used as the vacuum source.

The concentrated aerosol is then introduced into an aerosol collector 405 that either collects aerosol using electrostatic or inertial impaction or a combination of both. As described above sampled aerosol is then collected onto the front surface of an aerosol generator 415. In this embodiment the aerosol generator 415 contains an integrated optical sensor that provides a means for the surface detection of auto-fluorescence and optical reporter(s) emission from its front surface. A liquid thin-film is applied to the front surface of the aerosol generator 415 using one or more fluid delivery systems 460 and 470 before, during, or after aerosol is collected. An example of a fluid delivery system is a syringe pump containing a three port valve, automated control of the syringe pump's dispensing rate and syringe refill and reservoir(s) for storage of the optical reporter(s) or reporter precursor(s) and the necessary support reagents. In a preferred embodiment, the aerosol generator's front surface is planar with a diameter less than 0.5", preferably 0.2" in diameter or less. It is further preferred that bonded to the rear surface of generator 415 is an annular thermal cycling device that permits the exit of aerosol from generator 415 into air intake 420 and also provides a means for both rapidly cooling and/or heating the front surface of generator 415. This capability serves as an aid in reaction kinetics for some optical reporter(s) or reporter precursor(s), a means for denaturing proteins and doubletranded deoxyribonucleic and ribonucleic acid molecules, a means for assisting in the lysis of cellular and spore-type particles, and provides a means for performing nucleic acid type assays on the collected aerosol particles.

During the collection of aerosol, the integrated optical sensor can be configured to measure auto-fluorescence or optical reporter emission at one or more emission ranges. After a pre-determined period of time, or after a signal is generated indicating the presence of a particular substance, the aerosol generator 415 expels the reacted and non-reacted aerosol and the supporting reagents into a waste reservoir providing a regenerated surface, and the cycle of aerosol collection, detection and regeneration is repeated again. A signal processor 480 is used to process the auto-fluorescence and optical reporter emission signals detected by measuring the front surface of the aerosol generator 415. The main microcontroller 475 is used to control the vacuum pump 490, aerosol generator 410, fluid delivery systems 460 and 470, and the real-time airborne optical sensor 430.

Using the aerosol detection platforms described herein, there are numerous homogeneous assays that could be performed for the detection of biological, chemical, or radiological aerosols. For biological homogeneous assays there is a large body of literature describing different homogeneous assay techniques. For the purpose of applying these types of assays to biological aerosol detection and identification, such techniques can be summarized into the following classes: dye indicator, enzymatic, immunological, and nucleic acid type assays. Some useful resources are: "Conn's Biological Stains 10th Edition" edited by R. W. Horobin and J. A. Kiernan, "Handbook of Fluorescent Probes and Research Products" by Richard P. Haugland, "Flow Cytometry 3rd Edition" edited by Michael G. Ormerod, and "Flow Cytometry: First Principles 2nd Edition" by Alice Longobardi Givan. For all of the above classes, it is the purpose of this invention to select assays that produce fluorescence, phosphorescence, chemi-luminescence, or induce a color change upon reaction of an optical reporter with the analyte of interest.

There are a couple types of dye indicator assays that could be used for the detection platforms described in FIGS. 6, 7 and 8 for the detection and classification of sampled aerosol particles. The preferred responses for dye indicator assays are those that exhibit either a weak, or no optical effect until the indicator dye binds to the biological macromolecule. One type involves the non-covalent interaction of a dye with a biological macromolecule such as proteins, lipids, carbohydrates or nucleic acid polymers. For this type, either an enhancement in the fluorescence emission of the optical reporter is observed upon binding to a specific analyte, or a change of color is observed. Another type of a dye indicator assay involves either a fluorogenic or chromogenic reaction of the dye or dye precursor with the analyte producing a fluorophore or a chromophore that exhibits different absorbance properties than its precursor.

Another type of biological homogeneous assay is an enzymatic assay that utilizes one or more fluorogenic or chromogenic enzyme substrates to detect the presence of certain enzymes found in the biological particles of interest. For fluorogenic substrates, the optical reporter precursor is a fluorophore precursor that becomes fluorescent upon catalytic conversion to a fluorophore by an enzyme found in the sampled particle. For chromogenic substrates, a change in color is observed upon the catalytic conversion of the chromogenic substrate to a chromophore by an enzyme found in the sampled particle. For both of these types of enzyme substrates numerous assays exist and the above detection system platforms described in FIGS. 7 and 8 can be configured for specific detection of such optical reporters. One-step homogeneous immunoassays can also be used with the above detection platform, as described in FIG. 7, for immunological detection of antigens specific for a biological particle of interest. For these types of assays, an optical reporter is conjugated to an antibody specific towards an antigen found on the surface of a biological particle of interest. The optical reporter is a fluorophore or a phosphorescent molecule or particle. For cellular and spore-type biological particle detection, it is expected that multiple antigen sites are available for binding with the reporter-labeled antibody. This effectively produces a concentrated fluorescent or phosphorescent signal on the surface of the sampled particles, and, when re-aerosolized, these particles are detected one at a time in a manner similar to the way immuno-fluorescence techniques are applied in liquid flow cytometry. The fluorescent reporters can be either individual dye molecules conjugated to antibody, fluorescent or phosphorescent nanospheres or microspheres, quantum dots, or some other type of photo-luminescent nanocrystal.

The last type of biological homogeneous assay that can be used for biological aerosol detection using the detection platform described in FIG. 7 is a nucleic acid assay. The detection platform described in FIG. 7 provides an integrated aerosol collection and sample preparation method that is suitable for nucleic acid detection using fluorescent or phosphorescent probe techniques. The combination of a small impaction surface, small reagent volumes required for the front surface of the aerosol generator, a fast thermal transfer surface for DNA and RNA denaturation and nucleic acid probe hybridization, and the re-aerosolization of micron diameter volumes, creates a suitable environment for performing nucleic probe assays on genomic DNA and RNA. Using this detection platform, unamplified genomic DNA and RNA and amplified DNA/RNA detection can be performed. For unamplified genomic DNA/RNA detection, there are numerous homogeneous assays that can be performed such as, for example, the use of FRET based molecular beacons, two-color fluorescent probe detection, competitive fluorescent and phosphorescent based probe techniques. For target DNA or RNA sequence amplification there are numerous techniques that can be used for generating an optical response. A useful resource for nucleic acid amplification techniques is "DNA Amplification: Current Technologies and Applications" edited by Vadim V. Demidov and Natalia E. Broude.

EXAMPLES

Example 1

Example 1 provides a means for the detection and classification of the following airborne particulates: bacterial cells, bacterial spores, viral aggregates, protein toxin aggregates, mold spores, insect debris, plant cell debris and paper particulates. Two optical reporters are used to discriminate bacterial cells, bacterial spores, viral aggregates, and protein toxin aggregates from mold spores, insect debris, plant cell debris and paper particulates. Calcofluor White 2MR, Blankophor or UVITEX 2B are used to detect particulates containing cellulose or chitin. These dyes are excitable in the violet region, are fast reacting, and fluoresce upon binding to cellulose or chitin. The use of one of these optical reporters provides a means for discriminating mold spores, insect debris, plant cell debris and paper particulates from biological particulates that do not contain cellulose such as bacterial cells, bacterial spores, viral aggregates, and protein toxin aggregates. These dyes are excitable in the 350-420 nm range with fluorescence emission in the range of 400-470 nm.

Another optical reporter is employed that is specific for proteins. A protein specific optical reporter is used to enhance the lower detection limit of the detector to detect single cell and spore particles and to enhance the discrimination of bacterial cells, bacterial spores, viral aggregates and protein toxin aggregates from non-biological fluorescing aerosol. Red or near-IR excitable dyes are used for this detection channel and some examples are NN-127, a squarylium dye that is excited at 660 nm with a fluorescence emission of 690-790 nm, and indocyanine green dye (ICG), a dye that is excited at 785 nm with a peak emission at 820 nm. Other near-IR dyes are C-7, C-10 or C-12 developed by Gabor Patonay at Georgia State University with an excitation wavelength of 785 nm and a fluorescence emission of 790-860 nm. These dyes become strongly fluorescent upon the non-covalent binding to proteins.

When using the detection system layout described in FIG. 6, the two optical reporters are introduced as aerosols to the sampled aerosol, either generated as an aerosol separately or dispersed using the same solution and syringe pump. In one embodiment, the optical reporter aerosol is applied continuously to the sampled aerosol. In another embodiment, the optical reporter aerosol is introduced on a periodic basis such as, for example, once per minute for a period of thirty seconds or so. In another embodiment, the optical reporter aerosol is introduced only when triggered by the presence of a population of aerosol containing certain properties such as an elevated presence of auto-fluorescent aerosol, an elevated particle count, or elevated level of particles with certain absorption properties measured by differential elastic scatter. For all three embodiments, after coagulation of the optical reporter aerosol with the sampled aerosol has occurred, the coagulated aerosol is then introduced into an aerosol reaction zone providing a time delay of 1-30 seconds to allow for sufficient time for the optical reporters to react with surface cellulose or chitin, for the dyes calcofluor white 2MR, Blankophor or UVITEX or with surface protein, for the dyes NN-127, Indocyanine Green, C-7, C-10, or C-12. The reacted and non-reacted aerosol is then drawn into an airborne particle optical sensor using a sensor configuration as described in Diagrams 9, 10, or 11. In one embodiment, the sensor is configured to alternate the detection of untreated and treated sampled aerosol by synchronizing the output of the aerosol generator used for optical reporter coating with aerosol detection. Using this approach the aerosol sensor can be configured to measure particle size in the 0.5-10.0 micron diameter range, auto-fluorescence and/or differential elastic scatter for a period of time, for example, for thirty seconds. Then the aerosol sensor switches over to the optical reporter detection mode and measure's particle size in the 0.5-10.0 micron diameter range and the intensity level of the two optical reporters for each particle in this size range. To achieve this one or two detection channels are dedicated to detecting elastically scattered light at two excitation wavelengths, 405 nm and 660 nm or 785 nm (depending on which optical reporter dye is used for protein detection). Two elastic scatter detection channels are used if differential elastic scatter measurements are being performed. If not, only one elastic scatter detection channel is used for the purpose of particle sizing. Depending on the aerosol sensing configuration one or two detection channels is used for detecting both auto-fluorescence and the two optical reporter channels.

Using the aerosol sensing configuration illustrated in FIG. 9, a single detector is used to detect both the auto-fluorescence emission of flavins and the fluorescence emissions of the two optical reporters, the cellulose/chitin specific dyes having an emission range of 420-500 nm and the protein dyes having an emission range of 690-790 nm for NN-127 and 795-900 nm for indocyanine green, C-7, C-10, C-12. A multiband optical filter is used that is selective for two wavelength ranges: 420-580 nm for sensing both auto-fluorescence and cellulose/chitin dye fluorescence and 690-790 nm or 795-900 nm for the protein dye fluorescence. The intensity level of the cellulose/chitin dye fluorescence is used to separate auto-fluorescence from the dye fluorescence plus the fact the sensor detects auto-fluorescence at a different time than the cellulose/chitin dye fluorescence. The detection of both types of optical reporters is accomplished by either modulating the output of the two excitation sources to a frequency that permits the illumination of each aerosol event with both excitation wavelengths or by measuring a population with one source then the other. Whichever mode is used the signals generated from the fluorescence detection channel are synchronized with the source modulation so that the optical reporter fluorescence can be tracked to the appropriate reporter.

Using the aerosol sensing configuration illustrated in FIG. 10, two separate fluorescence detection channels are used permitting the simultaneous use of both the 405 nm and 660 nm sources with the subsequent simultaneous detection of both optical reporters for each aerosol event. As in the configuration described above, the auto-fluorescence is measured at a separate time from the optical reporter fluorescence and the fluorescence intensity levels are designed to be greater than the auto-fluorescence levels if cellulose or chitin material is present on the sampled particle.

Using the aerosol sensing configuration illustrated in FIG. 11, a single elastic scatter channel is used to measure particle size using any one of the sources. Two separate fluorescence channels are used: one configured for 420-580 nm emission for sensing both flavin fluorescence and the cellulose/chitin dye fluorescence and one configured for protein dye fluorescence with one of two emission ranges 690-790 nm or 795-900 nm. As with the preceding configuration, this permits the simultaneous use of both the 405 nm and 660 nm sources with the subsequent simultaneous detection of both optical reporters for each aerosol event.

Using the detection system layout illustrated in FIG. 7, aerosol is collected onto the front surface of a planar aerosol generator or onto another surface and then liquid transported the the front surface of the aerosol generator. In one embodiment, the optical reporter is applied continuously to the sampled aerosol and the reacted and un-reacted particles are re-aerosolized into the sensor's airstream. In another embodiment, the optical reporter aerosol is introduced to the collected particles on a periodic basis such as, for example, once per minute for a period of thirty seconds or so and then the reacted and un-reacted particles are re-aerosolized into the sensor's airstream. In another embodiment, the collection of aerosol with the subsequent introduction of optical reporters to the collected aerosol occurs only when triggered by the presence of a population of aerosol containing certain properties such as an elevated presence of auto-fluorescent aerosol, an elevated particle count, or elevated level of particles with certain absorption properties measured by differential elastic scatter. The reacted and un-reacted aerosol can then be measured using any of the above sensor configurations described above.

Using the detection system layout illustrated in FIG. 8, aerosol is collected onto the front surface of a planar aerosol generator or onto another surface and then liquid transported the front surface of the aerosol generator. In one embodiment, the optical reporter is applied continuously to the sampled aerosol and the reacted and un-reacted particles are measured on the front surface of the aerosol generator. After a predetermined period of time, the front surface of the aerosol generator is regenerated by aerosolizing the collected sample so that another collection cycle can be initiated. In another embodiment, the optical reporter aerosol is introduced to the collected particles on a periodic basis such as, for example, once per minute for a period of thirty seconds or so and the reacted and un-reacted particles are measured on the front surface of the aerosol generator. After measurement, the front surface of the aerosol generator is regenerated by aerosolizing the collected sample so that another collection cycle can be initiated. In another embodiment, the aerosol is collected onto the front surface of the aerosol generator and the auto-fluorescence of the collected aerosol is monitored using a 405 nm excitation source and the fluorescence detector with a 420-580 nm band optical filter. When a sufficient auto-fluorescence level is measured the optical reporters are applied and the optical reporters' fluorescence is measured.

The sensing configuration is comprised of two sources with excitation wavelengths of 405 nm and 660 nm or 785 nm. The sources are directed to illuminate the front surface of the aerosol generator and the fluorescence emission is measured for each of the two optical reporters using either a single detector and switching the sources on at different times or by using two fluorescence detectors equipped with optical filters selective towards the two emission ranges: 420-580 nm for the cellulose/chitin dye fluorescence and 690-790 nm or 795-900 nm for the protein dye fluorescence.

Example 2

Example 2 provides a means for the autofluorescence detection of airborne particulates by exciting particles at 266-300 nm and 350-490 nm and the detection of a protein specific optical reporter using a dye called fluorescamine. Excitation at 266-300 nm provides a means for the detection of aromatic amino acids commonly found in proteins, of which are universally present in biological particles. Excitation at 350-490 nm provides a means for the detection of NADH and flavins which are also commonly found in biological particles. The protein dye fluorescamine is a fast acting fluorogenic dye that when excited at 405 nm provides an intense fluorescence emission from 420-580 nm. The detection system layouts and aerosol sensing configurations described in Example 1 can be applied in the same manner in this example.

This example shows a benefit for the enhanced discrimination of bacterial cells, bacterial spores, viral aggregates, and protein toxin aggregates from paper particulates and organic carbon partilcuates and provides a means for enhancing the lower detection limit of single bacterial cells and spores. Discrimination of biological particulates from fluorescing paper particulates offers a means for the low level real-time detection of biological hazards in the mail sorting process.

Example 3

Example 3 provides a means for the autofluorescence detection of airborne particulates by exciting particles at 405-420 nm and the detection of a protein specific optical reporter using a protein specific dye called fluorescamine. Excitation at 405-420 nm provides a means for the detection of flavins which are also commonly found in biological particles. The protein dye, fluorescamine, is a fast acting fluorogenic that when excited at 405 nm provides an intense fluorescence emission from 420-580 nm. The detection system layouts and aerosol sensing configurations described in Example 1 can be applied in the same manner in this example.

As with Example 2, Example 3 provides a means for the discrimination of bacterial cells, bacterial spores, viral aggregates, and protein toxin aggregates from paper particulates, a means for enhancing the lower detection limit of single bacterial cells and spores, and a means for the specific detection of protein containing airborne particulates. As in Example 2, discrimination of biological particulates from fluorescing paper particulates offers a means for the low level real-time detection of biological hazards in the mail sorting process.

Example 4

Example 4 provides a means for the autofluorescence detection of airborne particulates by exciting particles 405-420 nm and the detection of a protein specific optical reporter using a dye called fluorescamine. A second excitation wavelength is employed at 660 nm for exciting another protein specific optical reporter called NN-127. Excitation at 405-420 nm provides a means for the detection of flavins of which are commonly found in biological particles. The protein dye, fluorescamine, is a fast acting fluorogenic dye that when excited at 405 nm provides an intense fluorescence emission from 420-580 nm. NN-127 is a noncovalent dye that becomes fluorescent upon binding to proteins with a fluorescence emission of 690-790 nm. The detection system layouts and aerosol sensing configurations described in Example 1 can be applied in the same manner in this example.

Example 5

Example 5 provides a means for the autofluorescence detection of airborne particulates by exciting particles 405-420 nm and the detection of a protein specific optical reporter using a dye called fluorescamine. A second excitation wavelength is employed at 785 nm for exciting one of the following protein specific optical reporters: indocyanine green, C-7, C-10, or C-12. Excitation at 405-420 nm provides a means for the detection of flavins of which are commonly found in biological particles. The protein dye, fluorescamine, is a fast acting fluorogenic dye that when excited at 405 nm provides an intense fluorescence emission from 420-580 nm. Indocyanine green, C-7, C-10, or C-12 are noncovalent dyes that become fluorescent upon binding to proteins with a fluorescence emission of 795-900 nm. The detection system layouts and aerosol sensing configurations described in Example 1 can be applied in the same manner in this example.

Example 6

Example 6 provides a means for the detection of radioactive airborne particulates. Liquid scintillators are used for the detection of alpha, beta, gamma, and neutron radiation. Anthracene can be used as an optical reporter which fluoresces upon the absorption of alpha, beta, gamma or neutron radiation with an emission range of 360-450 nm. This type of detection can be used for the detection of aerosols generated from the detonation of a "dirty bomb" and other radioactive aerosols. The detection system layouts and aerosol sensing configurations described in Example 1 can be applied in the same manner in this example with the exception that no excitation source is required for sensing this type of treated aerosol. By measuring fluorescing aerosol events with a fluorescence emission range of 360-450 nm in the absence of an excitation source radioactive aerosols may be detected.

I claim:

1. A system for detecting, classifying, and identifying an airborne particle comprising:
    A reaction zone for reacting a pre-selected marker on an airborne particle within the reaction zone;
    An optical reporter or reporter precursor selected based on reactivity with the pre-selected marker;
    A fluid delivery system for delivering the optical reporter or the reporter precursor as an aerosol or vapor to the reaction zone, wherein the optical reporter or reporter precursor is selected for its ability to react with the pre-selected marker on the airborne particle;
    At least one excitation source to generate and emit discrete wavelengths directed to the airborne particle;
    A detector that detects at least one of fluorescence, phosphorescence, chemi-luminescence signals or a combination thereof; and
    A signal processor for receiving signals from the detector that measures particle properties substantially in real time.

2. The system of claim 1 further comprising at least two excitation sources.

3. The system of claim 1 wherein the excitation source emits wavelengths in the range of about 220-300 nm.

4. The system of claim 1 wherein the excitation source emits wavelengths in the range of about 340-490 nm.

5. The system of claim 1, wherein the optical reporter is selected to react with a biological marker selected from the group consisting of: total protein, specific protein or peptide; amino acids; double stranded deoxyribonucleic acid (DNA); single stranded deoxyribonucleic acid; ribonucleic acid (RNA); specific enzymes; specific DNA or RNA sequences; other biological macromolecules; and combinations thereof.

6. The system of claim 1, wherein the optical reporter is selected to react with a radioactive particle to produce a fluorescence response.

7. The system of claim 1, wherein the optical reporter is a fluorophore or a phosphorescent molecule.

8. The system of claim 1, wherein the optical reporter has a fluorescence emission range of 365 nm to 445 nm in the presence of radioactive aerosols emitting radiation selected from the group consisting of gamma, neutron, beta, alpha radiation and combinations thereof.

9. The system of claim 1 further comprising a plurality of detectors wherein at least one detector is dedicated to detecting elastic scatter at one or more excitation wavelengths, and at least one detector is dedicated to detecting, at one or more excitation wavelengths, a condition selected from the group consisting of: auto-fluorescence; reporter-induced fluorescence; phosphorescence; and chemiluminescence.

10. The system of claim 1 wherein the excitation source produces particle excitation ranges selected from the group consisting of: from about 267 nm to about 300 nm; from about 350 nm to about 490 nm; and from about 530 nm to about 1500 nm.

11. The system of claim 1, wherein the reporter is selected from the group consisting of: squarylium dyes; indocyanine green; and combinations thereof.

12. The system of claim 1, wherein the optical reporters are selected from the group consisting of: cellulose reporters; chitin reporters; protein-specific optical reporters, and combinations thereof.

13. The system of claim 1, wherein airborne particles are selected from the group consisting of: bacteria cells, bacterial spores, viral aggregates and protein toxin aggregates, and combinations thereof.

14. The system of claim 1, further comprising:
 a first detector for detecting elastically scattered light at one excitation wavelength, from about 350 nm to about 490 nm and second detector for detecting auto fluorescence at a wavelength of from about 420 nm to about 580 nm and for detecting reporter-induced fluorescence at a wavelength of from about 420 nm to about 580 nm.

15. A system for detecting, classifying, and identifying an airborne particle comprising:
 a collection zone for collecting an airborne particle, the airborne particle having a pre-selected marker;
 a thin-film containing optical reporters or reporter precursors, wherein the optical reporter or reporter precursor is selected for its ability to react with the pre-selected marker on the airborne particle;
 a delivery system for delivering the airborne particle to the thin film;
 at least one excitation source to generate and emit discrete wavelengths directed to the particle;
 a detector that detects at least one of, fluorescence, phosphorescence, chemi-luminescence signals or a combination thereof;
 a signal processor for receiving signals from the detector that measures particle properties substantially in real time.

16. The system of claim 15 further comprising an aerosol generator.

17. The system of claim 16 wherein the delivery system is configured to apply a liquid thin-film to the front surface of the aerosol generator.

18. The system of claim 16 wherein the aerosol generator comprises a vibrating member having a front and rear surface and one or more tapered holes.

19. The system of claim 15 further comprising an aerosol concentrator.

20. The system of claim 15 further comprising at least two excitation sources.

21. The system of claim 15 wherein the excitation source emits wavelengths in the range of about 220-300 nm.

22. The system of claim 15 wherein the excitation source emits wavelengths in the range of about 340-490 nm.

23. The system of claim 15, wherein the optical reporter is selected to react with a biological marker selected from the group consisting of: total protein, specific protein or peptide; amino acids; double stranded deoxyribonucleic acid (DNA); single stranded deoxyribonucleic acid; ribonucleic acid (RNA); specific enzymes; specific DNA or RNA sequences; other biological macromolecules; and combinations thereof.

24. The system of claim 15, wherein the optical reporter is selected to react with a radioactive particle to produce a fluorescence response.

25. The system of claim 15, wherein the optical reporter is a fluorophore or a phosphorescent molecule.

26. The system of claim 15, wherein the optical reporter has a fluorescence emission range of 365 nm to 445 nm in the presence of radioactive aerosols emitting radiation selected from the group consisting of gamma, neutron, beta, alpha radiation and combinations thereof.

27. The system of claim 15, further comprising a plurality of detectors wherein at least one detector is dedicated to detecting elastic scatter at one or more excitation wavelengths, and at least one detector is dedicated to detecting, at one or more excitation wavelengths, a condition selected from the group consisting of: auto-fluorescence; reporter-induced fluorescence; phosphorescence; and chemiluminescence.

28. The system of claim 15, wherein the excitation source produces particle excitation ranges selected from the group consisting of: from about 267 nm to about 300 nm; from about 350 nm to about 490 nm; and from about 530 nm to about 1500 nm.

29. The system of claim 15, wherein the reporter is selected from the group consisting of: squarylium dyes; indocyanine green; and combinations thereof.

30. The system of claim 15, wherein the optical reporters are selected from the group consisting of: cellulose reporters; chitin reporters; protein-specific optical reporters, and combinations thereof.

31. The system of claim 15, wherein airborne particles are selected from the group consisting of: bacteria cells, bacterial spores, viral aggregates and protein toxin aggregates, and combinations thereof.

32. The system of claim 15, further comprising:
 a first detector for detecting elastically scattered light at one excitation wavelength, from about 350 nm to about 490 nm and second detector for detecting auto fluorescence at a wavelength of from about 420 nm to about 580 nm and for detecting reporter-induced fluorescence at a wavelength of from about 420 nm to about 580 nm.

33. A system for detecting, classifying, and identifying an airborne particle comprising:

a collection zone for collecting an airborne particle, the airborne particle having a pre-selected marker;

an optical reporter or reporter precursor selected for its ability to react with the pre-selected marker;

a thin-film containing the optical reporters or reporter precursors;

a delivery system for delivering the airborne particle to the thin film;

at least one excitation source to generate and emit discrete wavelengths directed to the particle;

a detector that detects at least one of, fluorescence, phosphorescence, chemi-luminescence signals or a combination thereof;

a signal processor for receiving signals from the detector that measures particle properties substantially in real time.

* * * * *